(12) United States Patent
Hao et al.

(10) Patent No.: US 11,576,578 B2
(45) Date of Patent: Feb. 14, 2023

(54) SYSTEMS AND METHODS FOR SCANNING A PATIENT IN AN IMAGING SYSTEM

(71) Applicant: SHANGHAI UNITED IMAGING HEALTHCARE CO., LTD., Shanghai (CN)

(72) Inventors: Weiqiang Hao, Shanghai (CN); Zhuobiao He, Shanghai (CN); Mingchao Wang, Shanghai (CN); Yining Wang, Shanghai (CN); Yimo Guo, Cambridge, MA (US); Srikrishna Karanam, Cambridge, MA (US); Ziyan Wu, Cambridge, MA (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 183 days.

(21) Appl. No.: 16/844,036

(22) Filed: Apr. 9, 2020

(65) Prior Publication Data

US 2020/0268251 A1    Aug. 27, 2020

Related U.S. Application Data

(63) Continuation of application No. 15/317,373, filed as application No. PCT/CN2016/075233 on Mar. 1, 2016, now Pat. No. 11,020,022.

(30) Foreign Application Priority Data

Mar. 2, 2015    (CN) .......................... 201510092839.7

(51) Int. Cl.
*G06K 9/00*    (2022.01)
*A61B 5/00*    (2006.01)
(Continued)

(52) U.S. Cl.
CPC ............ *A61B 5/0037* (2013.01); *A61B 5/055* (2013.01); *A61B 5/1114* (2013.01);
(Continued)

(58) Field of Classification Search
CPC .................. G06T 2210/41; G06T 7/70; G06K 9/00255; G06K 9/00335
See application file for complete search history.

(56) References Cited

U.S. PATENT DOCUMENTS 6,079,876 A * 6/2000 Schuetz ................... A61B 6/08
378/205
6,724,922 B1    4/2004 Vilsmeier
(Continued)

FOREIGN PATENT DOCUMENTS

CN    202151380 U    2/2012
CN    103767722 A    5/2014
(Continued)

OTHER PUBLICATIONS

International Search Report in PCT/CN2016/075233 dated May 26, 2016, 5 pages.
(Continued)

*Primary Examiner* — Guillermo M Rivera-Martinez
(74) *Attorney, Agent, or Firm* — Metis IP LLC

(57) ABSTRACT

The present disclosure relates to systems and methods for scanning a patient in an imaging system. The imaging system may include at least one camera directed at the patient. The systems and methods may obtain a plurality of images of the patient that are captured by the at least one camera. Each of the plurality of images may correspond to one of a series of time points. The systems and methods may also determine a motion of the patient over the series of time points based on the plurality of images of the patient. The systems and methods may further determine whether the
(Continued)

patient is ready for scan based on the motion of the patient, and generate control information of the imaging system for scanning the patient in response to determining that the patient is ready for scan.

20 Claims, 21 Drawing Sheets

(51) Int. Cl.
  *A61B 5/11* (2006.01)
  *G06T 17/20* (2006.01)
  *A61B 5/055* (2006.01)
(52) U.S. Cl.
  CPC .......... *A61B 5/1128* (2013.01); *G06T 17/205* (2013.01); *G06T 2200/04* (2013.01); *G06T 2210/41* (2013.01)

(56) References Cited

U.S. PATENT DOCUMENTS

| | | | |
|---|---|---|---|
| 2001/0046316 A1 | 11/2001 | Miyano et al. | |
| 2002/0023652 A1 | 2/2002 | Riaziat et al. | |
| 2002/0118280 A1 | 8/2002 | Medlar et al. | |
| 2002/0188194 A1* | 12/2002 | Cosman | G06T 7/73 600/426 |
| 2002/0193686 A1* | 12/2002 | Gilboa | A61B 6/4441 600/424 |
| 2003/0130576 A1* | 7/2003 | Seeley | A61B 6/4441 600/426 |
| 2004/0015075 A1 | 1/2004 | Kimchy et al. | |
| 2004/0054248 A1 | 3/2004 | Kimchy et al. | |
| 2004/0081341 A1 | 4/2004 | Cherek et al. | |
| 2005/0256390 A1 | 11/2005 | Laux et al. | |
| 2005/0265516 A1 | 12/2005 | Haider | |
| 2007/0167801 A1 | 7/2007 | Webler et al. | |
| 2011/0178783 A1* | 7/2011 | Smith | G06T 17/10 703/2 |
| 2011/0188726 A1 | 8/2011 | Nathaniel et al. | |
| 2012/0289825 A1 | 11/2012 | Rai et al. | |
| 2013/0218024 A1* | 8/2013 | Boctor | A61B 8/0841 600/476 |
| 2013/0345718 A1 | 12/2013 | Crawford et al. | |
| 2014/0005484 A1 | 1/2014 | Charles | |
| 2014/0126699 A1 | 5/2014 | Lee | |
| 2014/0357989 A1* | 12/2014 | Hendriks | A61B 34/20 600/424 |
| 2015/0051489 A1 | 2/2015 | Caluser et al. | |
| 2015/0062303 A1* | 3/2015 | Hanson | H04N 13/296 348/47 |
| 2015/0157242 A1 | 6/2015 | Sabesan | |
| 2015/0217137 A1 | 8/2015 | Takahashi | |
| 2016/0012390 A1 | 1/2016 | Skaaksrud | |
| 2016/0128666 A1 | 5/2016 | Grasruck et al. | |
| 2016/0166333 A1* | 6/2016 | Wang | A61B 90/11 600/476 |
| 2016/0206203 A1* | 7/2016 | Yu | A61B 6/466 |
| 2016/0324677 A1 | 11/2016 | Hyde et al. | |
| 2017/0168124 A1* | 6/2017 | Ueda | H04N 9/3185 |
| 2017/0258526 A1* | 9/2017 | Lang | A61B 17/155 |
| 2018/0150960 A1 | 5/2018 | Derda et al. | |
| 2018/0270474 A1 | 9/2018 | Liu | |
| 2018/0325472 A1 | 11/2018 | Lin et al. | |
| 2019/0046130 A1 | 2/2019 | Imamura et al. | |
| 2019/0183321 A1 | 6/2019 | Teranuma | |
| 2019/0240508 A1 | 8/2019 | Friman et al. | |
| 2019/0243138 A1 | 8/2019 | Peltola et al. | |
| 2019/0321657 A1* | 10/2019 | Hale | A61B 5/1128 |
| 2020/0015911 A1 | 1/2020 | Yi | |
| 2020/0126272 A1* | 4/2020 | Baer-Beck | H04N 13/204 |
| 2020/0218922 A1 | 7/2020 | Chen et al. | |
| 2021/0118173 A1 | 4/2021 | Wu et al. | |

FOREIGN PATENT DOCUMENTS

| | | |
|---|---|---|
| CN | 104000588 A | 8/2014 |
| CN | 104224212 A | 12/2014 |
| DE | 102007017794 B3 | 12/2008 |
| GB | 2340716 A | 2/2000 |
| WO | 2013160489 A1 | 10/2013 |
| WO | 2014120734 A1 | 8/2014 |
| WO | 2016138851 A1 | 9/2016 |

OTHER PUBLICATIONS

Written Opinion in PCT/CN2016/075233 dated May 26, 2016, 6 pages.
The Extended European Search Report in European Application No. 16758466.3 dated Jul. 25, 2018, 40 pages.
Timothy F. Cootes et al., Active Shape Models—Their Training and Application, Computer Vision and Image Understanding, 61(1): 38-59, 1995.
Timothy F. Cootes et al., Active Appearance Models, IEEE Transactions on Pattern Analysis and Machine Intelligence, 23(6): 681-685, 2001.
Olaf Ronneberger et al., U-Net: Convolutional Networks for Biomedical Image Segmentation, Medical Image Computing and Computer-Assisted Intervention, 9351: 234-241, 2015.
First Office Action in Chinese Application No. 201510092839.7 dated Sep. 26, 2016, 16 pages.
The Second Office Action in Chinese Application No. 201510092839.7 dated Apr. 6, 2017, 17 pages.
Communication Pursuant to Article 94(3)EPC in European Application No. 16758466.3 dated Feb. 25, 2021, 7 pages.

\* cited by examiner

SYSTEMS AND METHODS FOR SCANNING A PATIENT IN AN IMAGING SYSTEM

CROSS REFERENCE TO RELATED APPLICATIONS

This application is a continuation-in-part of U.S. patent application Ser. No. 15/317,373, filed on Dec. 8, 2016, which is a U.S. national stage under 35 U.S.C. § 371 of International Application No. PCT/CN2016/075233, filed on Mar. 1, 2016, designating the United States of America, which claims priority of Chinese Patent Application No. 201510092839.7 filed on Mar. 2, 2015, which is hereby incorporated by reference in its entirety.

TECHNICAL FIELD

The present disclosure relates to medical imaging, more particularly, relates to systems and methods for automatic patient readiness detection in medical imaging.

BACKGROUND

Imaging systems, such as CT scanners, MRI scanners, PET scanners, are widely used for creating images of interior of a patient's body for medical diagnosis and/or treatment purposes. Generally, a region of interest (ROI) covering a portion of the patient's body, such as a limb or an internal organ, is selected before an imaging session starts. Data is then acquired from within the ROI and analyzed, giving swift and accurate diagnosis thereafter. Thus, to ensure high quality imaging and accurate diagnosis, the ROI must be properly targeted during imaging. Normally, before the scan, the patient may lie on a patient support and be required to get ready for scan (e.g., keep still). After the patient is in a still or substantially still state, the patient support may be directed to move the patient to a target position for scan. Conventionally, an operator (e.g., a doctor) of the imaging system may need to observe the patient and determine whether the patient is ready for scan, which may be inefficient and susceptible to human error or subjectivity. Therefore, it is desirable to provide systems and methods for automatic patient readiness detection, thereby obviating the need for human intervention, and improving the precision and efficiency of patient readiness detection.

SUMMARY OF THE INVENTION

In a first aspect of the present disclosure, provided herein is a positioning system. In some embodiments, the positioning system may include a position acquiring unit, a position processing unit, and a control unit. In some embodiments, the position acquiring unit may include one or more cameras. The camera(s) may be configured to monitor or communicate with an imaging object in real time. The position processing unit may be configured to process or analyze one or more images to produce an outcome. The control unit may be configured to generate control information based on the outcome. In some embodiments, the positioning system may be configured to compose a set of images and/or videos taken by the cameras into a panoramic rendering of the imaging object and its surrounding environment.

In some embodiments, one or more images may include at least one characteristic feature indicative of a patient position, and the positioning processing unit may be further configured to recognize the characteristic feature to determine the patient position.

In some embodiments, the control unit may be further configured to generate control information for defining an imaging protocol suitable for the patient position and may be capable of updating the control information pursuant to a change of the patient position.

In some embodiments, one or more images may include at least one characteristic feature indicative of a region of interest (ROI), and the positioning processing unit may be further configured to recognize the characteristic feature to determine the ROI. In some embodiments, the control unit may be further configured to generate control information for targeting the ROI.

In some embodiments, the positioning processing unit may be further configured to calibrate the one or more images to generate a calibrated display, and the control unit may be further configured to receive a selection of a region of interest (ROI) from the calibrated display and generate control information for targeting the ROI.

In some embodiments, one or more images comprising at least one characteristic feature indicative of a reference position and the positioning processing unit may be further configured to recognize the characteristic feature to determine the reference position. In some embodiments, the control unit may be further configured to generate the control information based on the reference position.

In some embodiments, one or more cameras may have overlapping fields of view, and the position processing unit may be further configured to compose the one or more images to generate a panoramic image.

In some embodiments, the positioning system may be configured to automatically recognize a patient position. In some embodiments, the positioning system may be configured to target a region of interest (ROI) on a patient's body during an imaging session. In some embodiments, the ROI may cover an imaging object or a portion thereof. In some embodiments, the positioning system may be configured to communicate with an imaging system. In some embodiments, the positioning system may be configured to process patient's positional information, including but not limited to information regarding the patient position and the ROI, to generate the control information. In some embodiments, the positioning system may send the patient's positional information to the imaging system. In some embodiments, the positioning system may be configured to communicate with a hospital information system. In some embodiments, the positioning system may enable an operator of an imaging system to monitor a patient's status in real time.

In a second aspect of the present disclosure, provided herein is a positioning system, and the positioning system may include a position acquiring unit, a position processing unit, and a control unit. In some embodiments, the positioning system may include one or more position sources and position probes. The position source(s) and position probe(s) are used to monitor the instant location of an ROI. In some embodiments, the positioning system may be configured to determine a distance between a pair of position probe and position source based on communication between them. In some embodiments, ultrasound distance sensing may be used to determine the distance between a pair of position probe and position source.

In some embodiments, each position probe may have a communication range, and be configured to terminate the non-contact communication between the position probe(s) and source(s) when a position source leaves the communication range, and to establish the non-contact communication when the position source enters the communication range of another position probe. In some embodiments, the non-contact communication may be conducted via ultrasound signaling.

In some embodiments, one or more position probes may include at least three position probes, and the control unit may be further configured to execute the control information.

In a third aspect of the present disclosure, provided herein is a method for positioning a patient for medical imaging. The method may include: obtaining one or more images of the patient; recognizing at least one characteristic marker from the images, and the characteristic marker is indicative of a region of interest (ROI); generating control information based on the characteristic marker; positioning the patient based on the control information.

In some embodiments, the images may further include surrounding environment of the patient, and the at least one characteristic marker is located in the surrounding environment.

In a fourth aspect of the present disclosure, provided herein is a method for positioning a patient for medical imaging. The method may include: setting a position source indicative of an ROI of the patient; establishing one or more position probes at known locations; measuring distances between the position source and the one or more position probes; calculating a location of the position source based on the measured distances; generating control information based on the calculated position of the position source; positioning the patient based on the control information.

In some embodiments, measuring distances between the position source and the one or more position probes may be performed by ultrasound distance sensing.

In some embodiments, the medical imaging used in the present disclosure may be selected from the group consisting of digital subtraction angiography (DSA), computed tomography (CT), computed tomography angiography (CTA), positron emission tomography (PET), X-ray imaging, magnetic resonance imaging (MRI), magnetic resonance angiography (MRA), single-photon emission computerized tomography (SPECT), ultrasound scanning (US), CT-MR, CT-PET, CE-SPECT, DSA-MR, PET-MR, PET-US, SPECT-US, transcranial magnetic stimulation (TMS)-MR, US-CT, US-MR, X-ray-CT, X-ray-MR, X-ray-portal, X-ray-US, Video-CT, and Vide-US.

According to another aspect of the present disclosure, a system for scanning a patient in an imaging system is provided. The imaging system may include at least one camera directed at the patient. The system may include at least one storage device including a set of instructions and at least one processor configured to communicate with the at least one storage device. When executing the set of instructions, the at least one processor may be configured to direct the system to perform the following operations. The system may obtain a plurality of images of the patient that are captured by the at least one camera. Each of the plurality of images may correspond to one of a series of time points. The system may also determine a motion of the patient over the series of time points based on the plurality of images of the patient, and determine whether the patient is ready for scan based on the motion of the patient. The system may further generate control information of the imaging system for scanning the patient in response to determining that the patient is ready for scan.

In some embodiments, the plurality of images of the patient may include at least one of an RGB image, a depth image, or an infrared radiation (IR) image.

In some embodiments, the determining the motion of the patient based on the plurality of images of the patient may include identifying at least one feature point representing at least one body landmark of the patient in the image for each of the plurality of images, determining a motion of the at least one body landmark over the series of time points based on the at least one feature point identified in each of the plurality of images, and determining the motion of the patient over the series of time points based on the motion of the at least one body landmark.

In some embodiments, the determining the motion of the patient based on the motion of the at least one body landmark may include determining whether the motion of the at least one body landmark exceeds a threshold, generating a mesh model representative of the patient based on the image for each of the plurality of images in response to determining that the motion of the at least one body landmark does not exceed the threshold, and determining the motion of the patient over the series of time points based on the mesh models corresponding to the plurality of images.

In some embodiments, the determining the motion of the patient based on the plurality of images may include generating a mesh model representative of the patient based on the image for each of the plurality of images, and determining the motion of the patient over the series of time points based on the mesh models corresponding to the plurality of images.

In some embodiments, the determining the motion of the patient based on the mesh models corresponding to the plurality of images may include determining a posture representation of the patient for each of the plurality of images based on the corresponding mesh model of the patient, and determining the motion of the patient over the series of time points based on the posture representations of the patient corresponding to the plurality of images.

In some embodiments, for each of the plurality of images, the determining the posture representation of the patient may include determining the posture representation of the patient based on at least one of a patient model, a posture representation determination model, or a kinematic chain model.

In some embodiments, the determining the motion of the patient based on the mesh models corresponding to the plurality of images may include identifying at least one vertex of the mesh model for each of the plurality of mesh models corresponding to the plurality of images, and determining the motion of the patient over the series of time points based on the at least one vertex of each of the plurality of mesh models.

In some embodiments, the determining whether the patient is ready for scan based on the motion of the patient may include determining whether the motion of the patient exceeds a threshold, and determining that the patient is ready for scan in response to determining that the motion of the patient does not exceed the threshold.

In some embodiments, the generating control information of the imaging system for scanning the patient may include determining a position of an ROI of the patient based on at least one of the plurality of images, and generating the control information of the imaging system for scanning the patient based on the position of the ROI of the patient.

In some embodiments, the patient may be placed on a patient support, and the at least one of the plurality of images may include 3D image data corresponding to a first view with respect to the patient. The determining a position of an ROI of the patient based on at least one of the plurality of images may include obtaining a position of each of the at least one camera relative to the patient support, generating projection image data of the patient based on the 3D image data and the position of the each of the at least one camera relative to the patient support, the projection image data corresponding to a second view with respect to the patient different from the first view, and determining the position of the ROI of the patient based at least part on the projection image data.

According to yet another aspect of the present disclosure, a method implemented on a computing device having at least one processor and at least one storage device for scanning a patient in an imaging system is provided. The imaging system may include at least one camera directed at the patient. The method may include obtaining a plurality of images of the patient that are captured by the at least one camera, each of the plurality of images corresponding to one of a series of time points. The method may also include determining a motion of the patient over the series of time points based on the plurality of images of the patient, and determining whether the patient is ready for scan based on the motion of the patient. The method may further include generating control information of the imaging system for scanning the patient in response to determining that the patient is ready for scan.

According to yet another aspect of the present disclosure, a non-transitory computer readable medium comprising at least one set of instructions for scanning a patient in an imaging system is provided. The imaging system may include at least one camera directed at the patient. When executed by at least one processor of a computing device, the at least one set of instructions causes the computing device to perform a method. The method may include obtaining a plurality of images of the patient that are captured by the at least one camera, each of the plurality of images corresponding to one of a series of time points. The method may also include determining a motion of the patient over the series of time points based on the plurality of images of the patient, and determining whether the patient is ready for scan based on the motion of the patient. The method may further include generating control information of the imaging system for scanning the patient in response to determining that the patient is ready for scan.

According to another aspect of the present disclosure, a system for scanning a patient in an imaging system is provided. The system may include at least one camera directed at the patient. The system may include at least one storage device including a set of instructions and at least one processor configured to communicate with the at least one storage device. When executing the set of instructions, the at least one processor may be configured to direct the system to perform the following operations. The system may obtain a position of each of the at least one camera relative to the imaging system, and image data of the patient captured by the at least one camera. The image data may correspond to a first view with respect to the patient. The system may also generate projection image data of the patient based on the image data and the position of each of the at least one camera relative to the imaging system. The projection image data may correspond to a second view with respect to the patient different from the first view. The system may further generate control information of the imaging system for scanning the patient based on the projection image data of the patient.

In some embodiments, the imaging system may further include a patient support for supporting the patient, and the position of each of the at least one camera relative to the imaging system may be represented by a position of each of the at least one camera relative to a patient support.

In some embodiments, the reference pattern may be a three-dimensional object. For each of the at least one camera, the determining the position of the camera relative to the patient support based on a representation of the reference pattern in the at least one reference image may include determining a first position of the camera relative to the reference pattern based on the representation of the reference pattern in the at least one reference image, obtaining a second position of the reference pattern relative to the patient support, and determining the position of the camera relative to the patient support based on the first position and the second position.

In some embodiments, the reference pattern may be a two-dimensional or one-dimensional object. For each of the at least one camera, the obtaining at least one reference image associated with the reference pattern captured by the camera may include obtaining a plurality of reference images associated with the reference pattern.

The plurality of reference images may be captured by the camera when the patient support is at different positions.

In some embodiments, the reference pattern may include at least one of a cube, a checker, or a cross-shaped graph.

In some embodiments, the generating projection image data of the patient may include determining a position of a virtual camera having the second view based on the position of each of the at least one camera relative to the patient support, and generating the projection image data of the patient by rendering the image data based on the position of the virtual camera.

In some embodiments, the second view may be parallel to or perpendicular to a surface of the patient support at which the patient is placed.

In some embodiments, the generating control information of the imaging system for scanning the patient may include determining a position of an ROI of the patient based on the projection image data, and generating the control information of the imaging system for scanning the patient based on the position of the ROI.

In some embodiments, the projection image data may include a plurality of projection images each of which corresponds to one of a series of time points, and the generating control information of the imaging system for scanning the patient may include determining a motion of the patient over the series of time point based on the plurality of projection images of the patient, determining whether the patient is ready for scan based on the motion of the patient, and generating control information of the imaging system for scanning the patient in response to determining that the patient is ready for scan.

In some embodiments, the at least one camera may include a plurality of cameras having overlapping fields of view, and the generating projection image data of the patient based on the image data and the position of each of the at least one camera relative to the imaging system may include generating panoramic image data relating to the patient based on the image data, and generating the projection image data of the patient based on the panoramic image data and the position of each of the at least one camera relative to the imaging system.

According to yet another aspect of the present disclosure, a method implemented on a computing device having at least one processor and at least one storage device for scanning a patient in an imaging system is provided. The imaging system may include at least one camera directed at the patient. The method may include obtaining a position of each of the at least one camera relative to the imaging system. The method may also include obtaining image data of the patient captured by the at least one camera, the image data corresponding to a first view with respect to the patient. The method may further include generating projection image data of the patient based on the image data and the position of each of the at least one camera relative to the imaging system, the projection image data corresponding to a second view with respect to the patient different from the first view. The method may also include generating control information of the imaging system for scanning the patient based on the projection image data of the patient.

According to yet another aspect of the present disclosure, a non-transitory computer readable medium comprising at least one set of instructions for positioning a patient in an imaging system is provided. The imaging system may include at least one camera directed at the patient. When executed by at least one processor of a computing device, the at least one set of instructions may cause the computing device to perform a method. The method may include obtaining a position of each of the at least one camera relative to the imaging system. The method may also include obtaining image data of the patient captured by the at least one camera, the image data corresponding to a first view with respect to the patient. The method may further include generating projection image data of the patient based on the image data and the position of each of the at least one camera relative to the imaging system, the projection image data corresponding to a second view with respect to the patient different from the first view. The method may also include generating control information of the imaging system for scanning the patient based on the projection image data of the patient.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
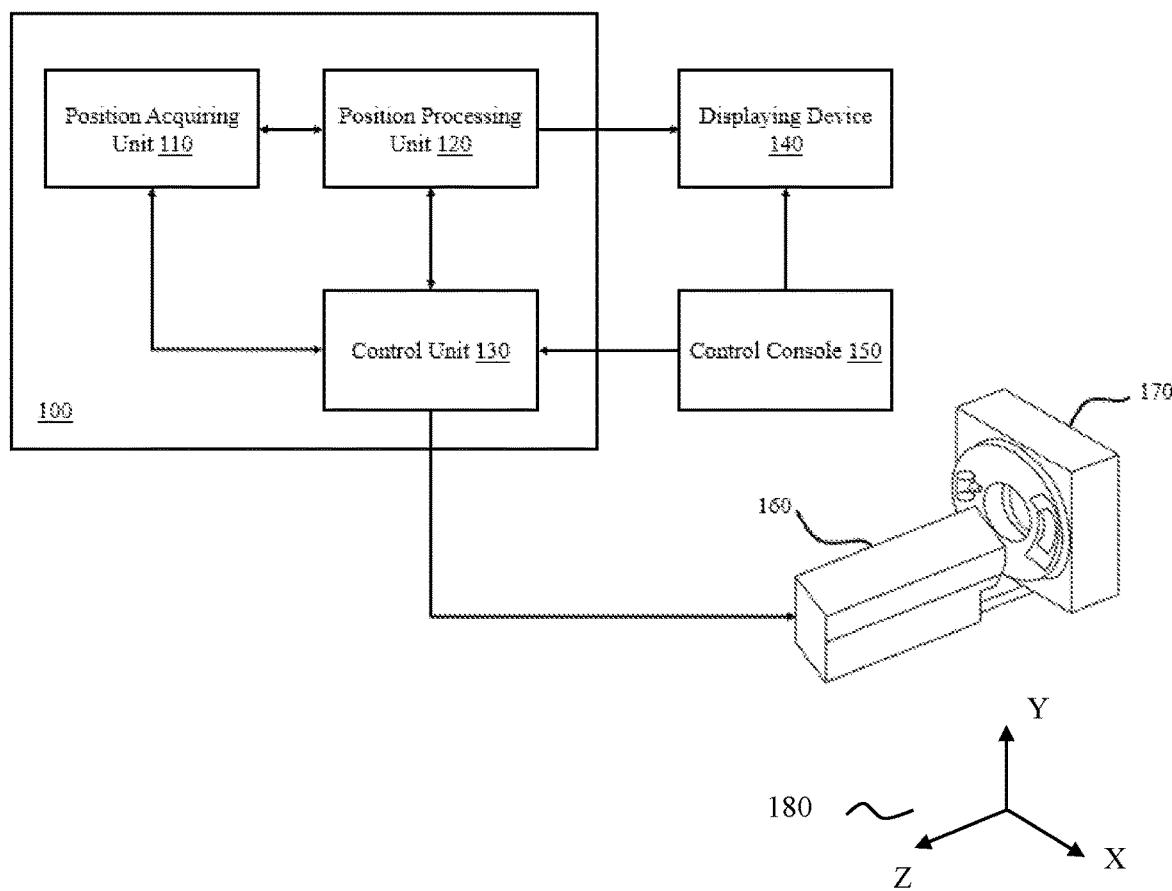
FIG. 1 illustrates an imaging system comprising a positioning system according to some embodiments of the present disclosure.

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

It will be understood that when a module or unit is referred to as being "on", "connected to", or "coupled to"

another module or unit, it may be directly on, connected, or coupled to the other module or unit or an intervening module or unit may be present. In contrast, when a module or unit is referred to as being "directly on," "directly connected to", or "directly coupled to" another module or unit, there may be no an intervening module or unit present. As used herein, the term "and/or" includes any and all combinations of one or more of the associated listed items.

The terminology used herein is for the purpose of describing particular example embodiments only and is not intended to be limiting. As used herein, the singular forms "a", "an", and "the" may be intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "pixel" and "voxel" in the present disclosure are used interchangeably to refer to an element of an image. In the present disclosure, the term "subject" and "object" are used interchangeably.

An aspect of the present disclosure may provide systems and methods for automatic patient readiness detection. The term "automatic" refers to methods and systems that carry out a process that analyzes information and generates results with little or no direct human intervention. The systems and methods may obtain a plurality of images of a patient that are captured by at least one camera. Each of the plurality of images may correspond to one of a series of time points. The systems and the methods may also determine a motion of the patient based on the plurality of images of the patient. The systems and the methods may further determine whether the patient is ready for scan based on the motion of the patient, and generate control information of the imaging system for scanning the patient in response to determining that the patient is ready for scan.

According to some embodiments of the present disclosure, the patient's readiness for scan may be detected by analyzing a plurality of images of the patient. Compared with a conventional approach that determines whether the patient is ready for scan by manually observing the patient, the systems and methods of the present disclosure may obviate the need for human intervention, and be insusceptible to human error or subjectivity. In addition, in some embodiments, the motion of the patient may be determined based on one or more body landmarks of the patient and/or a plurality of mesh models of the patient. For example, a two-level determination, which includes a first-level determination based on the body landmark(s) and a second level determination based on the mesh models, may be performed to improve the accuracy and reliability of the result of the readiness detection.

Another aspect of the present disclosure may provide systems and methods for scanning a patient in an imaging system, wherein the imaging system may include one or more camera directed at the patient. The systems and methods may obtain a position of each of the at least one camera relative to the imaging system and image data of the patient captured by the camera(s). The image data may correspond to a first view with respect to the patient. The systems and methods may further generate projection image data of the patient based on the image data and the position of each of the camera(s) relative to the imaging system. The projection image data may correspond to a second view with respect to the patient different from the first view. The systems and methods may also generate control information of the imaging system for scanning the patient based on the projection image data of the patient or a combination of the projection image data and the image data. For example, the position of an ROI may be determined based on the projection image data of the patient or a combination of the projection image data and the image data, and an instruction for controlling the imaging system may be generated such that the ROI may be targeted.

According to some embodiments of the present disclosure, projection image data corresponding to a different view of the patient may be rendered from the original image data, and the position of the ROI may be determined based at least in part on the projection image data. Merely by way of example, the original image data may represent a front view of the patient, which may be used to determine a position of the ROI on a frontal plane of the patient. The projection image data may represent a side view of the patient, which may be used to determine a position of the ROI on a sagittal plane of the patient. In this way, the position of the ROI in a 3D space may be determined, thereby improving the precision of the determined position of the ROI. Compared with a conventional approach that marking the ROI by a marker, the systems and methods of the present disclosure may improve the efficiency and precision of patient positioning and in turn, the accuracy and efficiency of the diagnosis and/or treatment performed based thereon.

In some embodiments, projection image data of the patient may be generated based on image data captured by a camera and a position of the camera with respect to the imaging system. For example, the position of the camera with respect to the imaging system may be represented by a position of the camera with respect to a patient support for supporting the patient. The present disclosure provides systems and methods for automatically determining the position of the camera with respect to the patient support based on a reference pattern placed on the patient support. For example, various reference patterns, such as a 3D reference pattern (e.g., a cube, a cuboid, a cylinder, a prism, etc.), a 2D reference pattern (e.g., a checker, a box, etc.), and/or a 1D reference pattern (e.g., one or more points, a line, etc.) may be utilized. Reference image(s) of the reference pattern may be captured for determining or calibrating the position of the camera relative to the patient support. Such methods of calibrating the position of the camera may be reliable and robust, insusceptible to human error or subjectivity, and/or fully automated. In addition, the reference pattern may have the advantages of simple structure, convenient manufacture, and low cost compared with other position measurement devices.

FIG. 1 illustrates an imaging system comprising a positioning system according to some embodiments of the present disclosure. In some embodiments, the positioning system 100 may be configured to automatically recognize a patient position. The term "patient position" as used herein refers to the physical positions of a patient's body, including the body's gesture, location within an imaging system, and orientation relative to components of the imaging system. For example, exemplary patient positions for a whole body scan include the supine, prone, right lateral recumbent, and left lateral recumbent positions. Further, in some embodiments, a patient position also includes information regarding the orientation of the body in the imaging system, such that the body is to be scanned in a certain direction, such as head to toe (e.g., head-first position), or toe to head (feet-first position).

In some embodiments, the positioning system 100 may be configured to target a region of interest (ROI) on a patient's body during an imaging session. The term "region of interest" or "ROI" as used herein refers to a subset of an image, a video, or a dataset identified for a particular purpose. Particularly, images and videos include but are not limited to 2-dimensional image (2D), three-dimensional (3D), and four-dimensional (4D) ones, as well as those covering a narrow or a panoramic field of view. Datasets as used herein refers to sets of values of qualitative or quantities variables in any form, including but not limited to a digital, analog, or wave form. Exemplary embodiments of an ROI pertaining to the present disclosure include a time interval for data acquisition, a frequency interval for waveform data, a spatial region defined by boundaries on or within an object or a representation thereof, including but not limited to images or drawings illustrating the object's contours, surfaces, or internal structures.

The term "target" as used herein refers to determining the ROI and/or acquiring data from within the ROI. Particularly, exemplary embodiments of targeting an ROI pertaining to the present disclosure include determining the ROI's form (e.g., a time interval or a spatial boundary), status (e.g., static or dynamic), location (e.g., in 3D space or on a 2D image), as well as positioning the ROI so as to acquire information (e.g., image or sound data) from within the ROI.

In some embodiments, the ROI may cover an imaging object or a portion thereof. The term "imaging object" as used herein broadly relates to any organic or inorganic mass, natural or man-made, that has a chemical, biochemical, biological, physiological, biophysical and/or physical activity or function. Exemplary embodiments of an imaging object pertaining to the present disclosure include cells, tissues, organs, or whole bodies of human or animal. Other exemplary embodiments include but not limited to man-made composition of organic and/or inorganic matters that are with or without life. In some embodiments, the imaging object may be a human patient. In some embodiments, the positioning system 100 may control the movement and positioning of an imaging object by controlling the movement of a support configured to carry the imaging object. In some embodiments, the support is a patient support 160 that is a part of an imaging system 170.

In some embodiments, the positioning system 100 may be configured to communicate with an imaging system 170. Imaging systems that can be used in connection with the present disclosure include components and combinations of single-modality or multi-modality imaging systems and devices, some of which are used for non-invasive diagnosis, intervention, and/or research in the biomedical field.

The term "imaging modality" or "modality" as used herein broadly refers to an imaging method or technology that gathers, generates, processes, and/or analyzes imaging information of a target body through a particular mechanism. Accordingly, a multi-modality imaging system of the present disclosure can include more than one imaging modality, such as two, three, or more different modalities. In a multi-modality system, the mechanisms through which different imaging modalities operate or function can be the same or different. Accordingly, the imaging information can also be the same or different. For example, in some embodiments, the imaging information can be internal and/or external information, and can be functional and/or structural information of the target body. Particularly, in some embodiments, the imaging information of different modalities complement one another, thereby providing a set of imaging data describing a target body from different analytical angles. For example, in some embodiments, the multi-modality imaging achieves merging of morphological and functional images.

In various embodiments, the imaging system may comprise imaging modalities for conducting various different medical scans or studies, including but not limited to digital subtraction angiography (DSA), computed tomography (CT), computed tomography angiography (CTA), positron emission tomography (PET), X-ray, magnetic resonance imaging (MRI), magnetic resonance angiography (MRA), single-photon emission computerized tomography (SPECT), ultrasound scanning (US), ultrasound scan, bone densitometry, or fluoroscopy. In various embodiments, exemplary multi-modality combination of the imaging system may include CT-MR, CT-PET, CE-SPECT, DSA-MR, PET-MR, PET-US, SPECT-US, TMS (transcranial magnetic stimulation)-MR, US-CT, US-MR, X-ray-CT, X-ray-MR, X-ray-portal, X-ray-US, Video-CT, or Vide-US.

Particularly, in some embodiments, the positioning system 100 may be configured to process patient's positional information, including but not limited to information regarding the patient position and the ROI, to generate control information. The imaging system 170 then receives the control information and performs the positioning procedure accordingly.

In some embodiments, the positioning system 100 may send patient's positional information to the imaging system 170. The imaging system 170 then processes the patient's positional information to generate control information and performs the positioning procedure accordingly.

In some embodiments, the positioning system 100 may be configured to communicate with a hospital information system (HIS; not shown in the figure). As used herein, the term "hospital information system" or "HIS" refers to the whole or part of a comprehensive, integrated information system designed to manage all aspects of a hospital's operation, such as the hospital's medical, administrative, financial, and legal issues, and the corresponding processing of services. In some embodiments, the positioning system 100 may send the patient's positional information or control information to the HIS. In some embodiments, the HIS may store and/or process information received from the positioning system 100. In some embodiments, the HIS may execute the control information to perform the positioning procedure. In some embodiments, the positioning system and/or the imaging system may be part of the HIS.

The term "control information" as used herein broadly relates to any information that directs operation of a system, including the positioning system and imaging system described herein. Exemplary embodiments of control information include information that specifies locations and/or directs movement of an ROI, an imaging object and/or one or more system components. In some embodiments, control information specifies a time, speed, path, angle, and/or instruction for moving an ROI, an imaging object, and/or one or more system components. In some embodiments, control information may be in the form of a machine-generated and/or user-input command that upon execution directs operation of the system, such as initiating a camera, running an algorithm, receiving, storing, or sending data, selecting an imaging protocol, and performing a positioning procedure, etc. The term "positioning procedure" as used herein refers to the process of placing an imaging object in a particular physical position relative to an imaging system during the operation of the system.

In some embodiments, the positioning system 100 may enable an operator of the system to monitor a patient's status in real time. Particularly, in some embodiments, the operator may input control information for the imaging system 170 to target a selected ROI. In some embodiment, an operator inputs control information via a control console 150. In some embodiments, the positioning system 100 is configured to execute the control information. Particularly in some embodiments, the positioning system 100, upon receiving the control information, may move and position the imaging object and one or more components of the imaging system 170 relative to one another, such that the ROI is targeted in the corresponding imaging session.

In various embodiments, system components moved and positioned during the positioning procedure include but are not limited to a support (e.g., a patient bed, a handle, etc.), a data acquisition device (e.g., an X-ray generator, a PET detector, etc.), a monitoring device (e.g., a camera, a lamp, etc.), a communication device (e.g., a microphone, a keypad, etc.), and a mechanical part (e.g., for carrying the system components, for adjusting a patient position, etc.). In some embodiments, during the positioning procedure, the system sends voice instruction for a patient to perform. It should be noted that the above examples are provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Structure-wise, in some embodiments, as shown in FIG. 1, the positioning system 100 may comprise a position acquiring unit 110. In some embodiments, the position acquiring unit 110 may include one or more cameras. In some embodiments, the camera(s) are used to monitor or communicate with an imaging object (such as a human patient) in real time. Particularly, in some embodiments, the camera(s) may be configured to capture images and/or videos of a patient near or in the imaging system 170. In some embodiments, the captured images and/or videos are used to monitor instant status of the patient, such as the patient's expression, gesture, and/or movement. In some embodiments, the captured images and/or videos are used for automatic patient position recognition. In some embodiments, the captured images and/or videos are used to assist ROI selection and targeting.

A camera used herein refers to any suitable device that is capable of capturing image data of the patient. Exemplary cameras may include a digital camera, an analog camera, a red-green-blue (RGB) sensor, an RGB-depth (RGB-D) sensor, a 3D scanner, a range device, a structured light scanner, a time-of-flight (TOF) device, a stereo triangulation camera, a sheet of light triangulation device, an interferometry device, a coded aperture device, a stereo matching device, an infrared radiation (IR) camera, or the like, or any combination thereof. The image data captured by a camera may include color image data, point-cloud data, depth image data, mesh data, IR image data, or the like, or any combination thereof, of the patient. The color image data may include color information, such as an RGB image of the patient. The point-cloud data may include a plurality of data points, each of which may represent a physical point on a body surface of the patient and include one or more feature values of the physical point (e.g., feature values relating to the position and/or the composition of the physical point). The depth image data refers to image data that includes depth information of each of a plurality of physical points on the body surface of the patient. The mesh data may include a collection of vertices, edges, and faces that defines a 3D shape of the patient. The IR image data refers to image data that includes temperature information of the body surface of the object.

In some embodiments, a camera may be a device independent from the imaging system 170. For example, the camera(s) may be mounted on a ceiling of a house where the imaging system 170 is placed. Alternatively, the camera(s) may be integrated into or mounted on the imaging system 170 (e.g., a gantry of the imaging system 170).

In some embodiments, multiple cameras may have a same or different field of view (FOV). For example, in some embodiments, one or more cameras may have an FOV covering a 90-180 degrees field. In some embodiments, one or more cameras may have an FOV covering 0-90 degrees field. In some embodiments, respective fields of view of multiple cameras may overlap.

In some embodiments, the positioning system 100 is configured to compose the set of images and/or videos taken by these cameras into a panoramic rendering of the imaging object and its surrounding environment. In some embodiments, the panorama is displayed to an operator of the system. As used herein, the term "panoramic" or "panorama" refers to an image or video that covers the maximum area of data acquisition of an imaging system, or an imaging object in its entirety, or an ROI in its entirety. In some embodiments, in addition to the imaging object or an ROI, a panorama also covers nearby environment where the imaging object or ROI is positioned. In some embodiments, a panorama has a field of view (FOV) of 0 to 45 degrees; in other embodiments, a panorama has a FOV of 45 to 90 degrees; in other embodiments, a panorama has a FOV of 90 to 180 degrees; in yet other embodiments, a panorama has a FOV of 180 to 360 degrees.

In some embodiments, the position acquiring unit 110 may comprise one or more position sources and probes. In some embodiments, the position source(s) and probe(s) are used to monitor the instant location of an ROI. Particularly, in some embodiments, the position sources and probes are configured to conduct non-contact communication. Particularly, in some embodiments, position sources may be configured to emit or receive a position signal, while position probes may be configured to receive or emit such position signal. In some embodiments, the position signal may be a non-contact signal of any form, including but not limited to an optical signal, a sound signal, or a magnetic signal. In some embodiments, a position source or a position probe may be placed on or near an ROI, thus the position signal may be used to determine the physical location of an ROI.

In some embodiments, the positioning system 100 is configured to determine a distance between a pair of position probe and source based on communication between them. Particularly, in some embodiments, a position source's physical location in a three-dimensional space may be calculated based on its distance to one or more position probe(s) of known physical location in the three-dimensional space. The number of position probe(s) needed for the calculation depends on the relative spatial relationship between the source and the probe(s).

In some embodiments, ultrasound distance sensing may be used to determine the distance between a pair of position probe and source. For example, in some embodiments, a position source configured to emit an ultrasound signal is placed near an ROI, while one or more position probe(s) configured to receive the ultrasound signal are placed at known positions of the imaging system. The distance between the source and the probe(s) can be calculated based on the time delay between when the source emits the signal and when the probe receives it.

It should be noted that the implementation of ultrasound distance sensing is provided merely for the purposes of illustration, and not intended to limit the scope of the present disclosure. As would be appreciated by skilled person in the art, other mechanisms for non-contact distance sensing could also be used in connection with the present disclosure. For example, in some embodiments, infrared distance sensing and/or laser distance sensing may be used. In some embodiments, multiple distance sensing mechanisms may be used in combination.

In some embodiments, positional information obtained by the positing acquiring unit 110 is transmitted to be processed by a module external to the positioning system 100, such as by a processor of the imaging system or the HIS. In other embodiments, positional information is processed locally by the positioning system 100. As shown in FIG. 1, in some embodiments, the positioning system 100 comprises a stand-alone position processing unit 120 configured for receiving and processing the positional information. In other embodiments, a position processing unit 120 may be integrated with other modules of the positioning system 100. For example, in some embodiments, the position acquiring unit 110 and the position processing unit 120 may be an integrated unit.

In some embodiments, the position processing unit 120 is configured to analyze an image and/or video of an imaging object, such as a human patient. Particularly, in some embodiments, the position processing unit 120 is configured to recognize patient position based on the image and/or video. In some embodiments, the position processing unit 120 is configured to generate panoramic images and/or videos of an imaging object. In some embodiment, the position processing unit 120 is configured to target an ROI of an imaging object and generate control information. In some embodiments, the position processing unit 120 is configured to transmit processed positional information or control information to external modules, including but not limited to a module of the positioning system 100, of the imaging system 170, or of an HIS.

According to the present disclosure, the position processing unit 120 may include any processor-based and/or microprocessor-based units. Merely by way of example, the processor may include a microcontroller, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or any combination thereof. The exemplary types of processors that may be used in connection with the present system are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

As shown in FIG. 1, in some embodiments, the positioning system 100 may further comprise a stand-alone control unit 130 configured for receiving and executing control information to perform a positioning procedure. In other embodiments, a control unit 130 may be integrated with other modules of the positioning system 100, such as integrated with the position acquiring unit 110, the position processing unit 120, or both. In various embodiments, control information received and executed by the control unit 130 may include machine-generated information, such as control information generated by the positioning system 100, an imaging system, or an HIS. Control information may also be input by a human operator of the system.

According to the present disclosure, the control unit 130 may include any processor-based and/or microprocessor-based units. Merely by way of example, the processor may include a microcontroller, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or any combination thereof. The exemplary types of processors that may be used in connection with the present system are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

As shown in FIG. 1, in some embodiments, the positioning system 100 may further comprise one or more displaying devices 140. In some embodiments, the displaying device(s) 140 may be configured to display, among other things, patient's positional information acquired and/or processed by the positioning system 100. Further, in some embodiments, based on the displayed information, a system operator may input control information for the imaging system to target a selected ROI.

According to the present disclosure, the displaying device 140 may be any suitable device that is capable of receiving, converting, processing, and/or displaying media content and/or performing any other suitable functions. For example, the displaying device 140 can be and/or include a Liquid Crystal Display (LCD) panel, Organic Light Emitting Diodes (OLED), a cathode ray tube (CRT) display, a plasma display, a touch-screen display, a simulated touch screen, or the like, or any combination thereof. In some embodiments, the displaying device 140 may be capable of three-dimensional (3D) displaying. In some embodiments, the displaying device 140 can be implemented as a touch-screen configured to detect a touch input pressure, a touch input position, or the like, or any combination thereof.

As shown in FIG. 1, in some embodiments, the positioning system 100 may further comprise a control console 150. In some embodiments, the control console 150 may be any suitable input device that is capable of inputting information to the positioning system 100. Exemplary input devices may include but are not limited to a keyboard, a mouse, a touch screen, a voice controller, or the like, or any combination thereof.

In some embodiments, two or more components of the positioning system 100 may be connected to each other via a wireless connection, a wired connection, or a combination thereof. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof.

It should be noted that the description of the positioning system is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope. For example, in some embodiments, the position processing unit 120 and the control unit 130 may be combined as a single unit.

Figure 2:
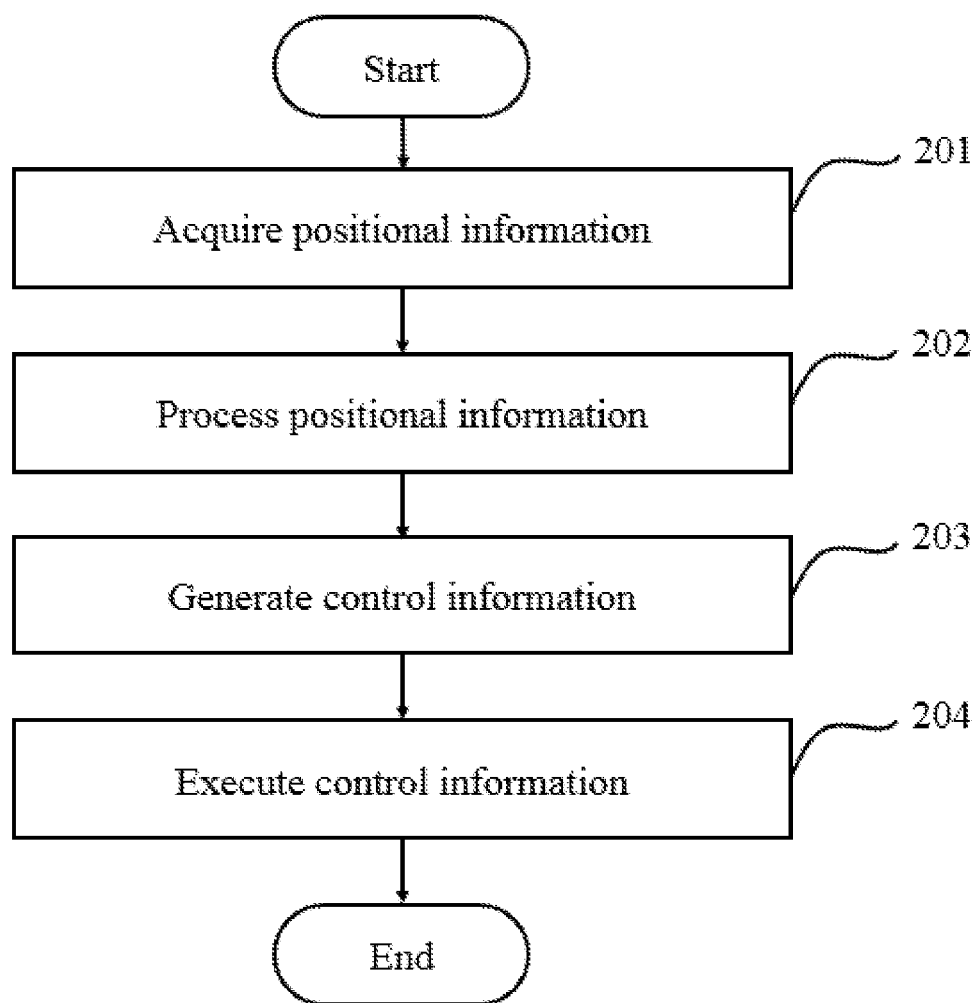
FIG. 2 is a flowchart illustrating a process performed by the present positioning system according to some embodiments of the present disclosure.

FIG. 2 is a flowchart illustrating a process performed by the present positioning system according to some embodiments of the present disclosure.

In step 201, positional information may be acquired. Exemplary mediums carrying the positional information may include images, videos, ultrasound, infrared beams, or any suitable medium for monitoring the status of a patient. Particularly, in some embodiments, the positioning system 100 comprises one or more cameras configured to monitor an imaging object and its surrounding environment. For example, in some embodiments, the cameras capture realtime images or videos of a patient lying on a patient support 160 of the imaging system 170.

In other embodiments, the positioning system 100 comprises pairing position sources and probes that are configured to communicate a position signal. For example, in some embodiments, one or more position sources are placed on a particular portion of a patient (e.g., near an ROI), and one or more position probes are placed at known locations. A position signal is transmitted between the position source(s) and position probe(s), thereby informing the positioning system 100 positional information of the imaging object. In various embodiments, the position signal may be ultrasound, infrared beams, or a combination thereof.

In step 202, positional information acquired in step 201 may be processed. In some embodiments, raw images and/or videos of an imaging object are processed. For example, in some embodiments, multiple cameras of the positioning system 100 are configured to capture a portion of a patient's body. In step 202, the set of images and/or videos may be composed into a panoramic rendering for showing on the displaying device 140. The panorama covers the patient's full body and the surrounding environment. In other embodiments, images of a patient may be analyzed for automatic recognition of the patient position. In yet other embodiments, the position signals transmitted between the position source and probe are analyzed to keep track of the instant location of an ROI.

In step 203, control information may be generated based on the positional information. The control information may include but is not limited to selection of an ROI for imaging and parameters for moving and positioning an imaging object and components of the imaging system such that the ROI can be properly targeted. For example, in some embodiments, an operator of the imaging system may manually set or update an ROI by selecting a portion on a displayed image. In other embodiments, the imaging system may automatically set or update the ROI, such as based on the recognized patient position. In other embodiments, an operator may manually input and/or the system may automatically generate various parameters for moving one or more system components (such as the patient support 160) to a suitable location, which parameters may include but are not limited to the distance, direction and speed of the movement. In yet other embodiments, an operator may manually input and/or the system may automatically generate or select protocols for controlling a subsequent imaging session, which parameters may include but are not limited to the method of image acquisition, duration, voltage, dosage, system components to be used in connection of the acquisition, and method of data processing, etc.

In step 204, the control information may be executed accordingly to perform a positioning procedure. For example, in a positioning procedure, an imaging object or one or more system components may be moved to a suitable location at a suitable speed. In various embodiments, system components moved and positioned during a positioning procedure include but are not limited to a support (e.g., a patient bed, a handle, etc.), a data acquisition device (e.g., an X-ray generator, a PET detector, etc.), a monitoring device (e.g., a camera, a lamp, etc.), a communication device (e.g., a microphone, a keypad, etc.), and a mechanical part (e.g., for carrying the system components, for adjusting a patient position, etc.). In some embodiments, during the positioning procedure, the system sends voice instruction for a patient to perform.

It should be noted that the flowchart above is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 3:
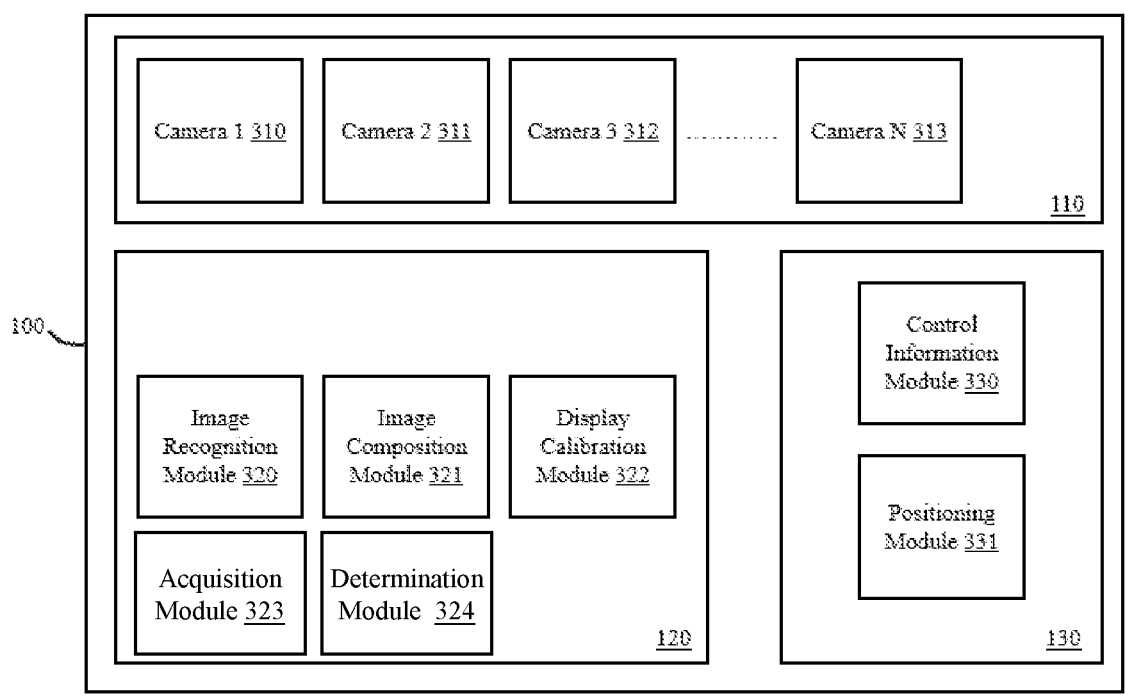
FIG. 3 is a block diagram of the positioning system according to some embodiments of the present disclosure.

FIG. 3 is a block diagram of the positioning system 100 according to some embodiments of the present disclosure. As shown in the figure, the positioning system 100 comprises a position acquiring unit 110, a position processing unit 120, and a control unit 130 as described in connection with FIG. 1 above.

Particularly, the position acquiring unit 110 may comprise one or more cameras for monitoring an imaging object. The cameras are labeled as camera 1 310, camera 2 311, camera 3 312, and camera N 313. The position processing unit 120 may comprise an image recognition module 320, an image composition module 321, an image calibration module 322, an acquisition module 323, and a determination module 324. The control unit 130 may comprise a control information module 330 and a positioning module 331.

According to the present disclosure, the camera(s) may be configured to monitor at least part of an imaging object and its surrounding environment. In some embodiments, the cameras may be mounted in the imaging gantry of an imaging system and configured to monitor a patient therein. Characteristics and setting of the camera(s) may vary according to a user's preference and practical needs. For example, if a medical practitioner needs to monitor a relatively small portion of a patient's body during an imaging session, such as the head or a limb, initiating a single camera of narrow FOV during the imaging session may suffice for the purpose. However, if a medical practitioner prefers to monitor the patient's entire body, a panoramic imaging solution may be used.

In some embodiment, the panoramic imaging solution may involve the use of a single camera, typically equipped with a wide to ultra-wide-angle lens. Exemplary wide-angle lenses include non-flat lenses and fisheye lenses. Selection of camera FOV involves a tradeoff between imaging coverage and quality. Particularly, as the camera FOV increases, the amount of imaging information and the size of a scene captured by the camera also increase. On the other hand, however, visual distortion also increases, as rendering the larger and larger amount of imaging information onto a flat image unavoidably requires more and more excessive stretching of pixels near borders of the image. The result is that produced panoramas may appear warped and do not correspond to a natural human view, which reduces authenticity and aesthetics of the image. In practice, flat panoramas start to look severely distorted once the camera FOV exceeds 90°. Thus, in some embodiments, the single-lens panoramic solution may be less preferred. Particularly, in those embodiments where the panoramic image is used for analyzing a patient position and/or positioning an imaging object or an ROI, visual distortion may negatively impact accuracy of the system.

An alternative solution is to use more cameras to cover a desirable total FOV, with each camera covering a smaller field without causing visual distortion. Thus, in some embodiments, the position acquiring unit 110 comprises a set of cameras. Particularly, each camera may be configured to capture at least part of a desired total FOV, such as an entire patient body and the patient support 160. Adjacent cameras' respective fields of view may overlap, such that the set of cameras together cover the desirable total FOV.

According to the present disclosure, the set of cameras may assume various different geometries as long as the captured set of images can be composed into a panorama covering a desirable total FOV. Particularly, the set of cameras may comprise any number of cameras. In some embodiments, the number of cameras may be greater than 1. Particularly in some embodiments, the number of cameras may range from 2 to 12. In some embodiments, the number of cameras may be any even number, such as 2, 4, 6, 8, 10, or 12 cameras. In some embodiments, the number of cameras may be any odd number, such as 3, 5, 7, 9, 10, or 11 cameras. Exemplary geometries of the camera set are described in details below in relation to FIGS. 5 and 6.

According to the present disclosure, camera(s) employed in the positioning system may be of various types and solutions. Exemplary cameras may include animation camera, autofocus camera, backup camera, banquet camera, box camera, bridge camera, camcorder, camera phone, closed-circuit television camera, compact camera, compact system cameras, dashcam, digital camera, disposable camera, document camera, field camera, firewire camera, folding camera, gun camera, helmet camera, high-speed camera, hidden camera, instant camera, IP camera, keychain camera, light-field camera, live-preview digital camera, medium format camera, mirrorless interchangeable-lens camera, monorail camera, movie camera, multiplane camera, omnidirectional camera, onboard camera, pinhole camera, pinspeck camera, plate camera, pocket camera, pocket video camera, point-and-shoot camera, pool safety camera, press camera, process camera, professional video camera, rapatronic camera, rangefinder camera, red light camera, reflex camera, remote camera, rostrum camera, schmidt camera, single-lens reflex camera, spy cam, spy camera, stat camera, stereo camera, still camera, still video camera, subminiature camera, system camera, thermal imaging camera (firefighting), thermographic camera, toy camera, traffic camera, traffic enforcement camera, twin-lens reflex camera, video camera, view camera, webcam, wright camera, zenith camera, zoom-lens reflex camera, or the like, or any combination thereof.

In some embodiments, the image composition module 321 may be configured to compose the set of images into a panoramic image. Depending on the geometry of how cameras are set around the imaging object and relative to one another, different image processing methods or algorithms may be used to generate the panorama. For example, in some embodiments, the imaging processing method registers set of images into alignment estimates, blends them in a seamless manner, and at the same time solves the potential problems such as blurring or ghosting caused by parallax and scene movements as well as varying image exposures. Particularly, in some embodiments, panorama composition may include registration, calibration and blending steps. Particularly, image registration may use the direct alignment method or the feature-based method to search for optimum alignments that minimize the sum of absolute differences between overlapping pixels of different images. Image calibration may be performed to minimize differences between an ideal lens model and the actual cameras and imaging condition, such as correcting optical defects, exposure differences, focus differences, vignetting, camera response, chromatic aberrations, blurring and ghosting, etc. Image blending may be performed based on the result of image calibration, and combined with remapping of the images to an output projection.

In some embodiments, panorama composition may involve the direct alignment method and/or the feature-based method. Particularly, using the direct alignment method, each pixel of a first image may be compared with that of a second image, so as to find the optimum cut-and-stitch line for composing the two images. Using the feature-based method, features of the two images may be extracted and compared, so as to find the optimum cut-and-stitch line. Exemplary feature detecting and abstraction methods may include Harris, Scale-Invariant Feature Transform (SIFT), Speeded Up Robust Features (SURF), Features from Accelerated Segment Test (FAST), PCA-SIFT, and ORB techniques. In some embodiments, algorithms including mean square distance, least square, Euclidian distance, the linear weighted algorithm, Gaussian-weighted algorithm, may be used for panorama composition. Exemplary embodiments of panorama composition are described in detail below in relation to FIGS. 7B and 7C.

In some embodiments, the display calibration module 322 may be configured to receive original images acquired by the position acquiring unit 110 or panoramic images generated by the image composition module 321, and further calibrate the images for displaying on the displaying device 140. Particularly, the display calibration module 322 registers positional information in physical space as corresponding positional information on a displayed image. Thus, when a system operator selects an ROI on a screen-displayed image, the positioning system 110 is able to translate the selection into a corresponding ROI in physical space. In some embodiments, the calibration may be based on a mapping relationship between the dimension of the panorama's total FOV and the dimension of the displayed image. An exemplary embodiment of the mapping relationship is described in detail below in relation to FIG. 9.

In some embodiments, the image recognition module 320 may be configured to perform image-based automatic inspection and analysis for such applications as automatic patient position recognition and ROI targeting. Particularly, in some embodiments, the image recognition module 320 is configured to recognize one or more human body features from a captured image or video, the body feature(s) being indicative of the patient position. In some embodiments, the image recognition module 320 is configured to recognize one or more position markers from a captured image or video, the position marker(s) being indicative of the position of an ROI. Exemplary embodiments of image recognition are described in detail below in relation to FIGS. 10 and 11.

In some embodiments, the acquisition module 323 may be configured to acquire information for patient readiness detection. For example, the acquisition module 323 may acquire a plurality of images of a patient, which may be captured by one or more cameras. Each of the images may correspond to one of a series of time points. More descriptions regarding the obtaining of the images may be found elsewhere in the present disclosure. See, e.g., operation 1810 and the relevant descriptions thereof.

The determination module 324 may be configured to determine a motion of the patient over the series of time points based on the images of the patient. For example, the determination module 324 may identify one or more feature points representing one or more body landmarks of the patient in each of the images. The body landmark(s) may include one or more representative body regions of the patient, such as one or more anatomical joints, a shoulder, an ankle, the waist, a knee, a groin, or the like, or any combination thereof. The determination module 324 may further determine the motion of the patient over the series of time points based on the feature points of the images. As another example, the determination module 324 may generate a mesh model representative of the patient based on each of the images, and determine the motion of the patient over the series of time points based on the mesh models corresponding to the plurality of images. More descriptions regarding the determination of the motion of the patient may be found elsewhere in the present disclosure. See, e.g., 1820 and relevant descriptions thereof. In some embodiments, the determination module 324 may be configured to determine whether the patient is ready for scan based on the motion of the patient. More descriptions regarding the determination as to whether the patient is ready for scan may be found elsewhere in the present disclosure. See, e.g., 1830 and relevant descriptions thereof.

In some embodiments, the acquisition module 323 may be configured to obtain a position of each of the camera(s) relative to the imaging system 170. For example, the position of a camera relative to the imaging system 170 may be represented by a position of the camera relative to a patient support for supporting the patient. More descriptions regarding the obtaining of the position of the camera(s) relative to the patient support may be found elsewhere in the present disclosure. See, e.g., operation 2010 and the relevant descriptions thereof. As another example, the acquisition module 323 may obtain image data of the patient captured by the camera(s), wherein the image data may correspond to a first view with respect to the patient. More descriptions regarding the obtaining of the image data corresponding to the first view of the patient may be found elsewhere in the present disclosure. See, e.g., operation 2020 and the relevant descriptions thereof. As yet another example, the acquisition module 323 may obtain at least one reference image associated with a reference pattern placed on the patient support. More descriptions regarding the obtaining of a reference image may be found elsewhere in the present disclosure. See, e.g., operation 2110 and the relevant descriptions thereof.

The determination module 324 may be configured to determine the position of the camera relative to the patient support based on the representation of the reference pattern in the at least one reference image. More descriptions regarding the determining the position of the camera relative to the patient support may be found elsewhere in the present disclosure. See, e.g., operation 2120 and the relevant descriptions thereof. Additionally or alternatively, the determination module 324 may be configured to generate projection image data of the patient based on the image data of the patient and the position of each of the camera(s) relative to the patient support. The projection image data may correspond to a second view with respect to the patient, which is different from the first view. More descriptions regarding the generating of the projection image data of the patient may be found elsewhere in the present disclosure. See, e.g., operation 2030 and the relevant descriptions thereof.

In some embodiments, the control information module 330 may generate control information based on results transmitted from the position processing unit 120. In some embodiments, the control information module 330 may be configured to receive a system operator's input. In some embodiments, a calibrated panoramic image may be displayed on the displaying device 140. An operator of the imaging system may select an ROI on the displaying device 140 by manipulating the displayed panoramic image. For example, the operator may select the ROI by drawing a pair of lines or an area on the displayed image. The control information module 330 may receive the selection, translate the selection into parameters corresponding to the ROI's location in physical space, and generate a set of control information.

In some embodiments, the control information module 330 may be configured to generate control information of the imaging system for scanning the patient. For example, the control information module 330 may determine a position of an ROI of the patient based on image data (e.g., the images corresponding to the time series, the image data corresponding to the first view of the patient, the projection image data, etc.) of the patient. Based on the position of the ROI of the patient, the control unit 130 may generate the control information of the imaging system for positioning the patient. The control information may include an instruction to move one or more components of the positioning system 100 and/or the imaging system 170 such that the ROI can be targeted.

The positioning module 331 may be configured to receive and execute the control information. For example, in some embodiments, the positioning module 331 may execute the control information to perform a positioning procedure. Particularly, in some embodiments, the positioning module 331, upon receiving and executing the control information, may move a patient to the parameter-specified position in the imaging gantry, such that the ROI may be targeted during the next imaging session.

It should be noted that the above description of the positioning system is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope. In some embodiments, two or more components of the positioning system may be integrated into a single component. A component of the positioning system may be implemented on two or more sub-components. For example, in some embodiments, the image recognition module 320, the image composition module 321, and the display calibration module 322 may be combined into a single functional unit. Additionally or alternatively, the positioning system may include one or more additional components and/or one or more components of the positioning system described above may be omitted.

Figure 4:
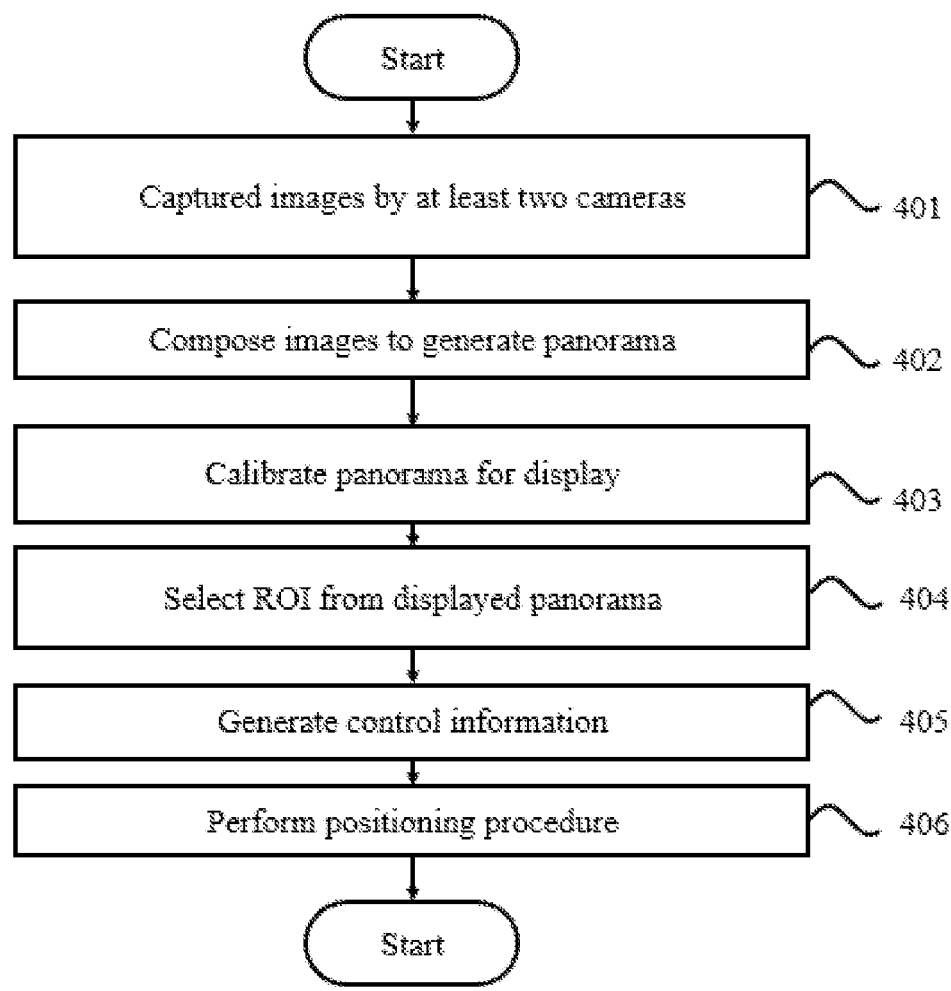
FIG. 4 is a flowchart illustrating an exemplary process of patient positioning according to some embodiments of the present disclosure.

FIG. 4 is a flowchart illustrating an exemplary process of patient positioning according to some embodiments of the present disclosure. In step 401, images captured by at least two cameras may be recognized. In some embodiments, each camera of the at least two cameras may be configured to monitor at least part of the imaging object. Two adjacent cameras of the at least two cameras may overlap in their respective FOV. In some embodiments, the cameras may be mounted inside an imaging gantry of an imaging system and configured to monitor a patient therein.

In step 402, images recognized in step 401 may be composed to generate a panoramic image that covers the entire imaging object and surrounding environment. Depending on the geometry of how cameras are set around the imaging object, different image-stitching algorithms may be used to generate the panorama.

In step 403, the panoramic image may be calibrated for displaying, such as on a displaying device 140 as described in connection with FIG. 1. The calibration algorithm registers positional information in physical space as corresponding positional information in the displayed image. Thus, when a system operator selects an ROI on a screen-displayed image, the system is able to translate the selection into a corresponding ROI in physical space. In some embodiments, the calibration may be based on a mapping relationship between the size of the panorama's total FOV and the size of the displayed image.

In step 404, an ROI may be selected based on the displayed panoramic image. In some embodiments, an operator of the imaging system may select an ROI either via the control console 150 or directly on the displaying device 140 by manipulating the displayed panoramic image. For example, the operator may select the ROI by drawing a pair of lines or an area on the displayed image.

In step 405, control information may be generated based on the ROI selection in step 404. In the calibration step, the system keeps track of positional correspondence between the displayed image and the physical space. Thus, in some embodiments, after an ROI is selected, the system is able to translate the selection into parameters corresponding to the ROI's location in physical space, and generate a set of control information.

In step 406, a positioning procedure may be performed. For example, in some embodiments, upon executing the control information, the system may move a patient to the parameter-specified position in the imaging gantry, such that the ROI may be targeted during the next imaging session.

It should be noted that the above flowchart is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 5:
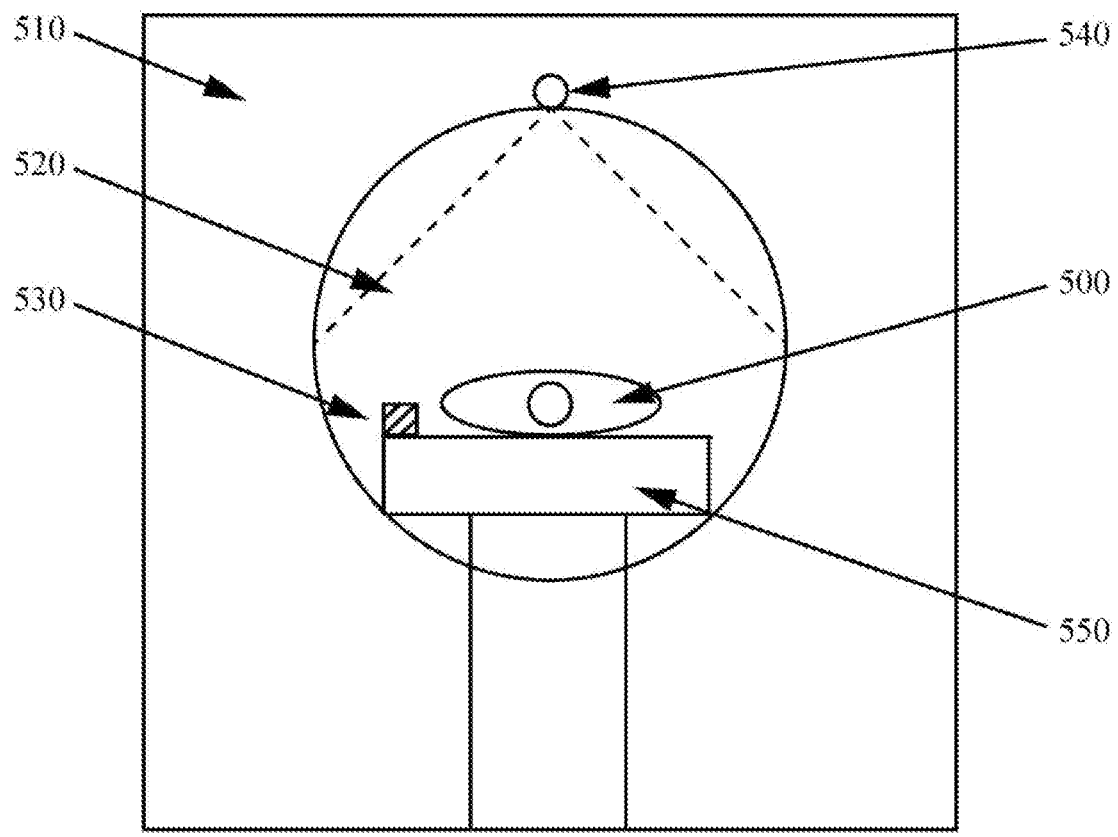
FIG. 5 is a schematic illustration of a cross-sectional view of the imaging system according to some embodiments of the present disclosure.
Figure 6:
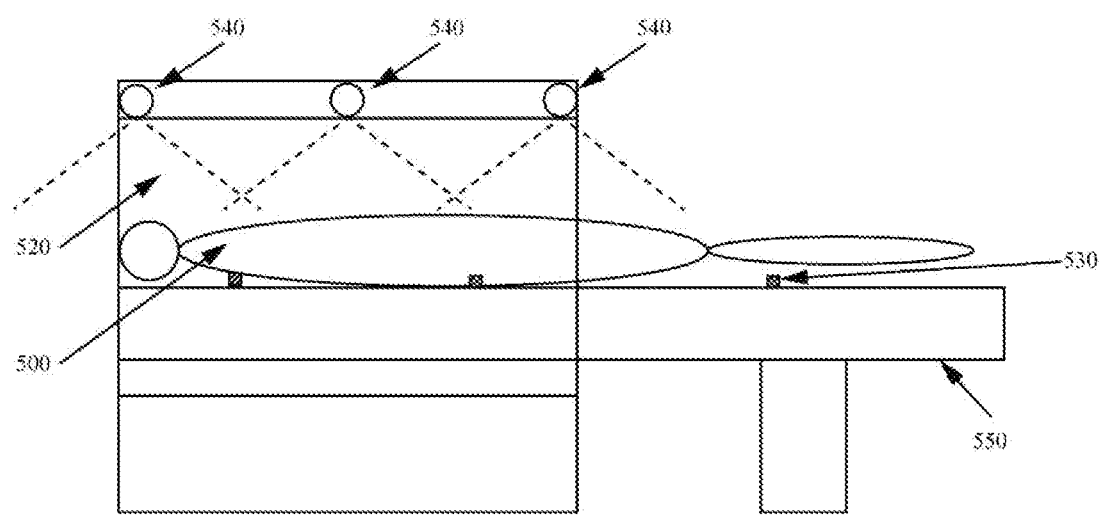
FIG. 6 is a schematic illustration of a side view of the imaging system according to some embodiments of the present disclosure.

FIGS. 5 and 6 illustrate exemplary embodiments of an imaging device equipped with a positioning system according to the present disclosure.

Particularly, FIG. 5 is a schematic illustration of a cross-sectional view of the imaging system according to some embodiments of the present disclosure. As can be seen from this view, a patient 500 lies on a patient support 550. The patient support 550 is configured to move the patient 500 in and out of an imaging gantry 520 of an imaging system 510. One or more reference pattern 530 is placed on the patient support 550. One or more camera 540 is placed in the imaging gantry 520 above the centerline of the patient's body.

FIG. 6 is a schematic illustration of a side view of the imaging system according to some embodiments of the present disclosure. As can be seen from this view, three cameras 540 are mounted inside the imaging gantry 520. A patient 500 is lying on the patient support 550. The cameras are arranged in a straight line above the center of the patient's body. Two adjacent cameras have an overlapping area in their respective FOV. Three reference patterns 530 are placed on the patient support 550.

In this particular embodiment, the three cameras 540 are mounted at the same vertical height from the patient support 550 and are arranged in a straight line with respect to one another. Particularly, the straight line may be parallel with the longitudinal axis of the patient support 550 moves. In some embodiments, the straight line may superimpose with the centerline of the patient's body 500; that is, the cameras 540 are mounted above the center of the patient's body 500. In some embodiments, the cameras 540 are distributed evenly in a straight line; that is, distances between adjacent cameras 540 are the same.

However, it can be now appreciated that a variety of embodiments of the position acquiring unit 110 may be employed. These embodiments may have different numbers and/or arrangements of cameras, but a common feature is that each camera's FOV overlaps with that of at least one other camera, thereby enabling the positioning system 100 to capture a desirable total FOV. Those of ordinary skills in the art upon reading the present disclosure should become aware of how a position acquiring unit according to the present disclosure can be designed to satisfy particular needs. Particularly, skilled persons in the art would follow the guidance provided by the present disclosure to select a suitable number of cameras with reasonable fields of view and arrange the set of cameras such that neighboring cameras' fields of view have reasonable overlap that enables the system to cover a desirable total FOV and reliably process image information in the overlapping field to produce panoramas. Some exemplary geometries of the set of cameras that may be employed are described further below.

Particularly, in some embodiments, the number of cameras may be less or more than 3. For example, in some embodiments, the system includes two or more lines of cameras aligned above a scanning area. Each line of cameras may or may not superimpose with the centerline of the scanning area. In some embodiments, overlapping FOV exists for adjacent cameras in the same line and/or in different lines.

In some embodiments, the cameras may not align in a straight line with respect to one another. For example, in some embodiments, the cameras may be scattered around an imaging object. In some embodiments, the set of cameras may be arranged in a curve or in a convex or concave surface, such as on the surface of a sphere.

In some embodiments, the cameras may not sit at the same vertical height from a reference plane, such as the patient support. For example, one camera may be placed at a lower position than other cameras, due to spatial constraint in the imaging gantry. In some embodiments, distances between adjacent cameras may not be the same. Particularly, in some embodiments, overlapping areas of different pairs of adjacent cameras may be of different size.

In some embodiments, camera FOV may range between 20° to 90°, such as 20°, 30°, 40°, 50°, 60°, 70°, 80°, and 90°. In some embodiments, camera FOV may be greater than 90°, such as 90°, 100°, 110°, 120°, 130°, 140°, 150°, 160°, 170°, and 180°.

Depending on the geometry of how cameras are set around the imaging object, different image-stitching algorithms may be used to generate the panorama. In the embodiments as shown in FIGS. 5 and 6, reference patterns are used to help to locate the overlapping areas in adjacent images. Particularly, one or more characteristic reference patterns may be placed in the overlapping FOV of adjacent cameras. These reference patterns thus are indicative of the physical range covered by a given camera, as well as an overlapping area that is captured in both adjacent images. Thus, based on the location of a reference pattern, adjacent images may be cut and stitched along the edge of the overlapping area to form a continuous image covering a larger total FOV.

Figure 7A:
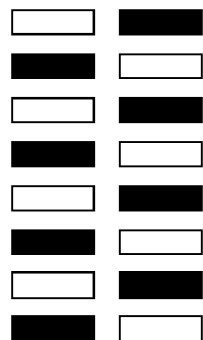
FIG. 7A illustrates an exemplary embodiment of a reference pattern that may be employed in the positioning system according to some embodiments of the present disclosure.

The reference pattern may have any combination of colors, shapes, and/or textures, including but not limited to black, white, grayscale, colorful, fluorescent; standard geometrical shapes such as circle, oval, triangle, square, trapezium, diamond, rhombus, parallelogram, rectangle, pentagon, hexagon, heptagon, oblong, octagon, nonagon, decagon, or the like; symbols such as star, heart, moon, arrow, stripe, ladder, or the like; icons or images such as a teddy bear, a national flag or the like; letters, barcodes, and characters; textures such as rough, smooth, heat-absorbing, heat-reflective, etc. Merely by way of example, FIG. 7A illustrates an exemplary embodiment of a reference pattern that may be employed in the positioning system according to some embodiments of the present disclosure. As shown in the figure, the reference pattern 700 comprises two columns of alternating black and white boxes.

In some embodiments, the reference patterns may be placed on the patient support. In other embodiments, the reference patterns may be placed in the coils of an MRI scanner.

Figure 7B:
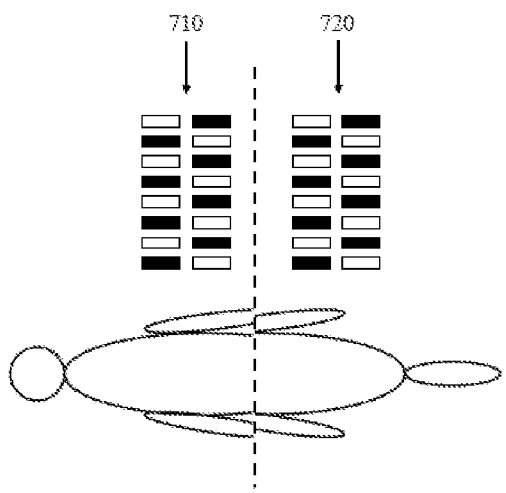
FIGS. 7B and 7C illustrate an exemplary method for panorama composition according to some embodiments of the present disclosure.
Figure 7C:
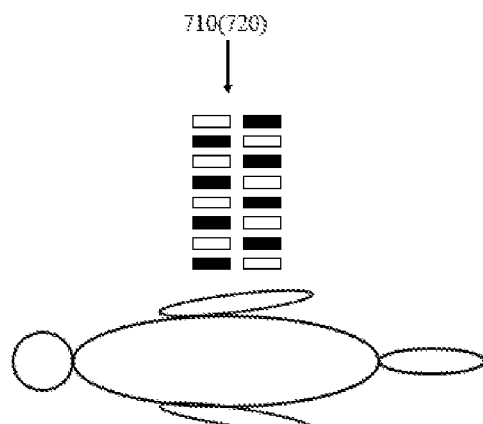

FIGS. 7B and 7C illustrate an exemplary method for panorama composition. Particularly, FIG. 7B shows a pair of adjacent images having an overlapping FOV. Both images capture the reference pattern in the overlapping FOV (710, 720). To find an optimum cutting-and-stitching line for composing the pair of images, the method firstly aligns the two images to the extent that the reference patterns (710, 720) as in the two images overlap completely. Then the overlapped area in one of the two images may be cut and the remaining portions of the images may be stitched together to produce the panorama as shown in FIG. 7C.

Figure 8:
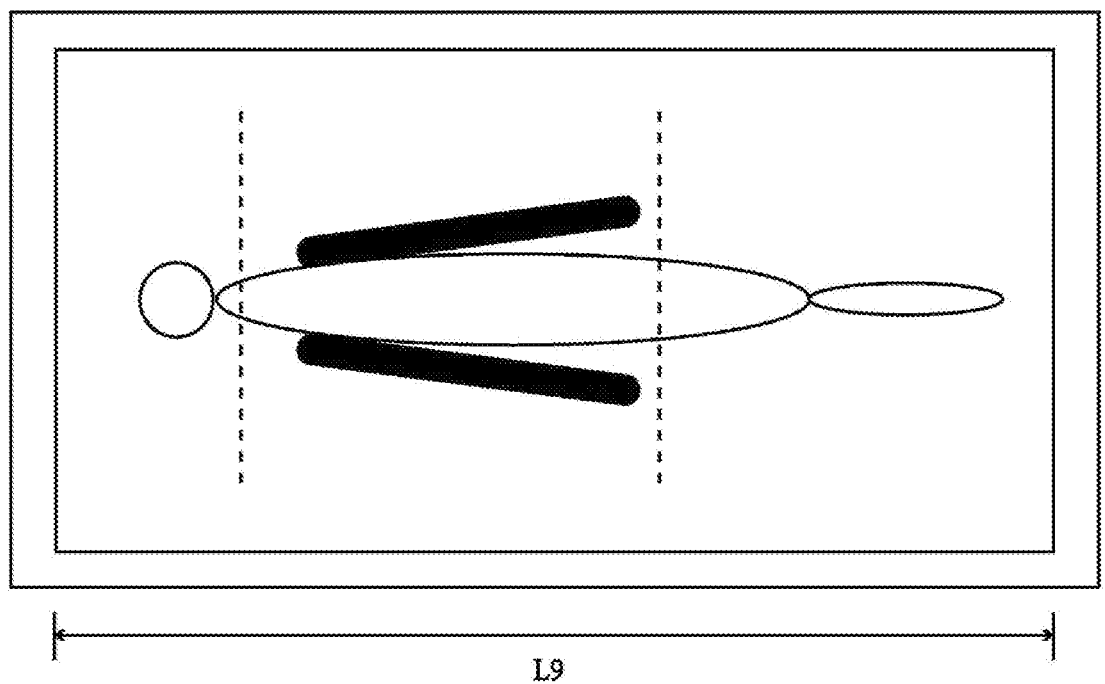
FIG. 8 illustrates a displaying device showing a calibrated panoramic image according to some embodiments of the present disclosure.

FIG. 8 illustrates a displaying device showing a calibrated panoramic image according to some embodiments of the present disclosure. As shown in the figure, a calibrated panoramic image may be shown on a display 800. In various embodiments, the display 800 may be embodied as a touch screen, or other suitable displaying devices. In this figure, L9 denotes a dimension of the displayed panorama.

An operator of the imaging system may select an ROI directly from the calibrated panoramic image by manipulating the display 800. In this particular embodiment, the operator draws a pair of lines flanking part of the patient's body as the ROI. In some embodiments, the operator may select an ROI via an input device, such as a keyboard or a mouse. In some embodiments, a rotary knob may be employed for fine adjustment of the position of the ROI selected by the operator. In some embodiments, the input devices may be integrated on the control console 150 as described in connection with FIG. 1. It should be noted that the calibrated panoramic image described above is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 9:
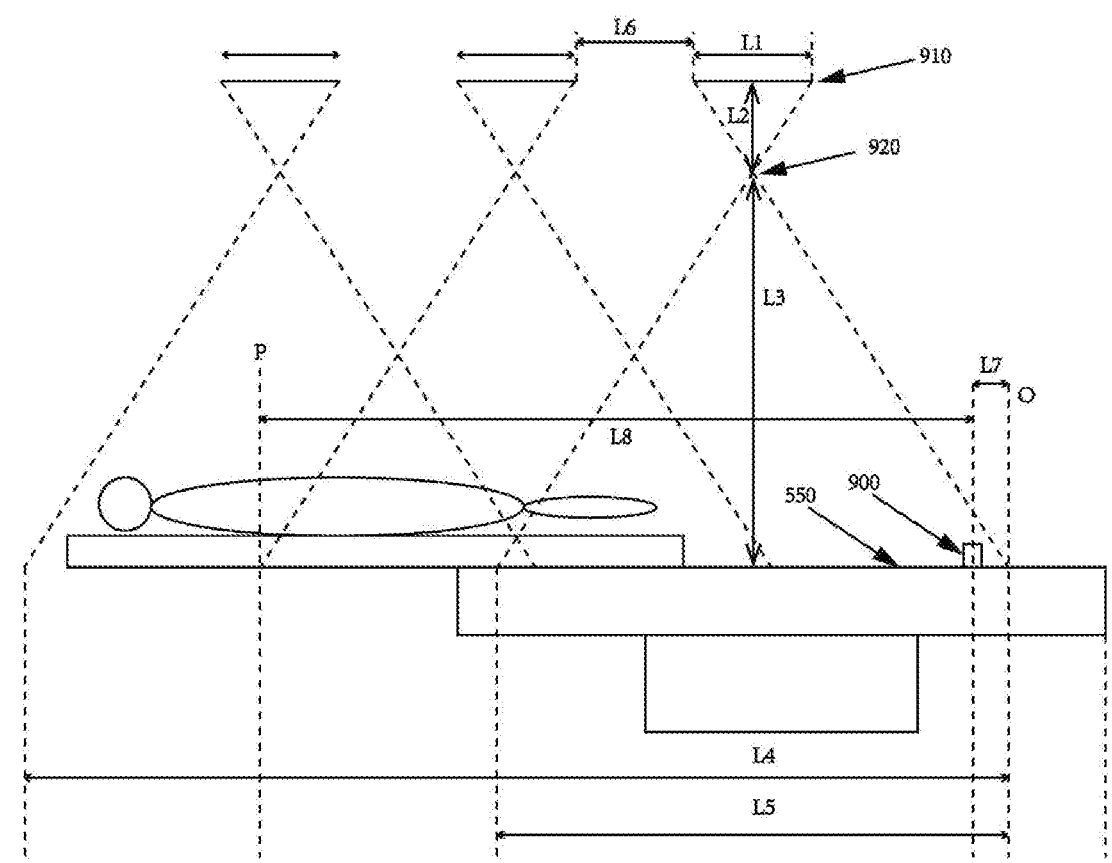
FIG. 9 illustrates exemplary procedure for calibrating an image and generating control information according to some embodiments of the present disclosure.

FIG. 9 illustrates exemplary procedures for calibrating an image and generating control information according to some embodiments of the present disclosure. Particularly, the image may be a single camera image or a multi-camera panorama.

In the embodiment shown in FIG. 9, the positioning system comprises multiple cameras having overlapping fields of view. Each camera may comprise an image sensor 910 and a lens 920. The cameras are mounted above the patient support 550 at the same height, and the cameras are arranged in a straight line. The straight line is parallel with the longitudinal axis of the patient support 550.

As shown in the figure, L1 denotes a dimension of the image sensor 910. L2 denotes the distance between the image sensor 910 and the lens 920. L3 denotes the distance between the lens 920 and the captured scene (for example, the patient support 550). L5 denotes a dimension of the captured FOV, which may change with L3. L6 denotes the distance between adjacent cameras. In this configuration, a ratio between the dimension of the image sensor 910 (L1) and the dimension of the captured FOV (L5) is L2/L3. Thus, L5 can be calculated as:

$$L5 = L1 * L3/L2 \qquad \text{(Equation 1)}$$

In some embodiments, calibrating the image for displaying may be based on a mapping relationship between the dimension of the captured FOV (L5) and the dimension of the displayed image (L9 as shown in FIG. 8). Particularly, the mapping relationship can be written as the ratio: L9/L5.

Optionally, the system of FIG. 9 may perform panoramic imaging using multiple cameras. Let N denote the number of cameras used in the panoramic imaging solution, and L4 denotes a dimension of the total panoramic FOV. In this configuration, L4 can be calculated as:

$$L4 = L5 + (N-1)*L6 + (N-1)*L1 \qquad \text{(Equation 2)}$$

Accordingly, the mapping relationship for calibrating the multi-camera panoramic image for displaying can be written as the ratio: L9/L4.

The dimension of the displayed image (L9) correlates with the size of an area used for displaying the image, such as on a screen. In some embodiments, a system operator may customize the displaying area, such as having the image displayed in full screen, or enlarged to display in extended double screens, or reduced to display in a half-screen window. Thus, the mapping relationship may remain constant or change during operation of the imaging system. In any case, the display calibration module 322 of the positioning system 100 keeps track of the instant mapping relationship during calibration.

As such, the calibration process registers positional information in physical space (e.g., L4) as corresponding positional information in the displayed image (e.g., L9). Thus, when an operator specifies a particular region of the displayed patient's body as the ROI, the positioning system is able to calculate the corresponding region in physical space, and generate control information for moving and/or positioning various components of the imaging system, including but not limited to the patient support 550, such that the corresponding physical region will be properly targeted during imaging.

For example, in the embodiment as shown in FIG. 9, the operator draws line P on the displayed image, which denotes the position where the scan should begin or end. To calculate the physical position of line P, in some embodiments, zero position 900 of known physical position is used as a reference point. Particularly, in some embodiment, zero position 900 is provided as a marker on the patient support 550. In some embodiments, a reference pattern may be used to denote zero position 900.

In some embodiments, a height of the patient support 550 is adjusted such that zero position 900 is within the total panoramic FOV, and thus is shown on the displayed image. Particularly, in the embodiment as shown in FIG. 9, line O denotes the edge of the total panoramic FOV that covers zero position 900. As shown in the figure, L7 denotes the physical distance between edge O and the zero position 900, and L8 denotes the physical distance between line P and zero position 900. Let L8' (not shown in the figure) denotes the displayed distance between line P and zero position 900. According to the mapping relationship described above, $$L8'/L8=L9/L4 \qquad \text{(Equation 3)}$$

As described above, the mapping relationship (L9/L4) and the displayed distance (L8') are known to the positioning system. Thus, the physical distance between line P and zero position 900 (L8) can be calculated. Further, because zero position 900 is known, the physical position of line P can be obtained.

Figure 10A:
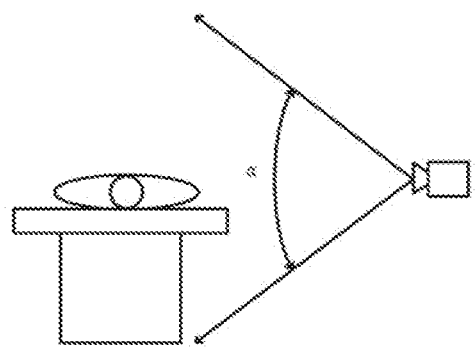
FIGS. 10A-10C illustrate exemplary locations of one or more cameras capturing a patient lying on a patient support according to the several embodiments of the present disclosure.
Figure 10B:
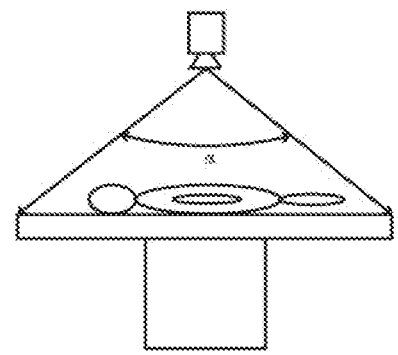
Figure 10C:
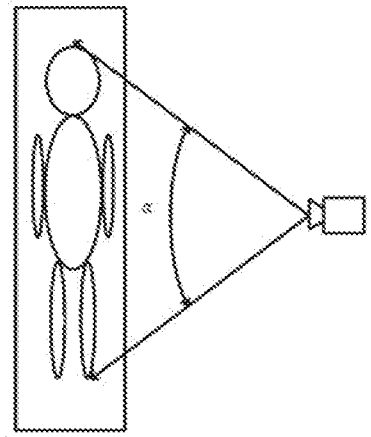
Figure 11:
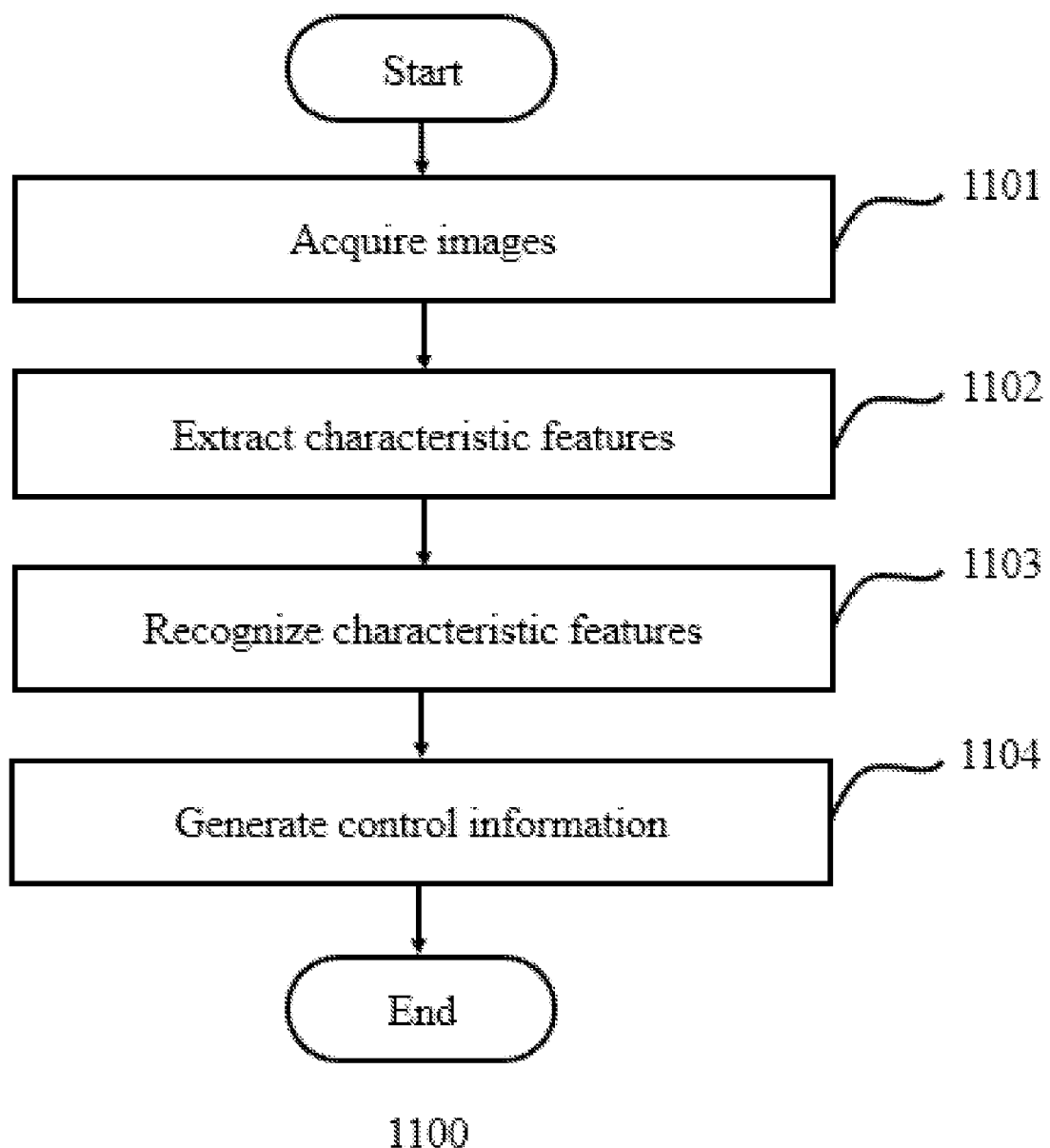
FIG. 11 illustrates an exemplary process of image recognition according to some embodiments of the present disclosure.

FIGS. 10 and 11 illustrate exemplary system components and procedure for image recognition according to several embodiments of the present disclosure. Depending on practical needs or user preferences, in various embodiments, the image and/or video for image recognition may be taken from various angles with respect to the imaging object; may cover the entire imaging object or certain feature-containing portions; may be a panoramic rendering or a narrow FOV rendering of the imaging object; and may be in 2D or 3D. For example, FIGS. 10A through 10O illustrate exemplary locations of one or more cameras capturing a patient lying on a patient support according to the several embodiments of the present disclosure. As shown in the figure, the camera may be placed at various locations and angles with respect to the patient. For example, as shown in FIG. 10A, a camera may be placed lateral to the patient support and captures a FOV ($\alpha$) that covers the vertical dimension of the patient. As shown in FIG. 10B, a camera may be placed above the patient support captures a FOV ($\alpha$) that covers the horizontal dimension of the patient. As shown in FIG. 10O, the camera may be installed lateral to the patient support and captures a FOV ($\alpha$) that covers the horizontal dimension of the patient. In some embodiments, these cameras may be initiated simultaneously or sequentially during image recognition. In some embodiments, one or more cameras may be only installed within a space where imaging takes place, such as installed inside an imaging gantry. Thus, the cameras are capable of monitoring and updating a patient's instant status during an imaging session.

FIG. 11 illustrates an exemplary process of image recognition according to some embodiments of the present disclosure. The method or process 1100 may be performed by processing logic that comprises hardware (e.g., cameras, patient support, circuitry, dedicated logic, programmable logic, microcode, etc.), software (e.g., instructions run on a processing device to perform hardware simulation), or a combination thereof. In some embodiments, one or more operations of the method 1100 can be performed by one or more computing and/or console devices (e.g., one or more computing and/or console devices as described above in connection with FIG. 1) to generate and execute control information automatically.

In step 1101, one or more images and/or videos of a patient assuming a patient position may be acquired. Depending on practical need or user preference, the one or more images and/or videos may be taken from different angles with respect to the patient; may cover the patient's entire body or certain feature-containing portions of the body, such as the face, limbs, back or chest.

In step 1102, characteristic features in the images are extracted. Pertaining to the present disclosure, characteristic features may include features of an imaging object itself and features in the surrounding environment of an imaging object.

Particularly, in some embodiments, characteristic features include human body features, such as facial features (e.g., eye or nose), body features (e.g., limb or chest), gender features (e.g., breast or laryngeal prominence), morphology features (e.g., lesion or tumor), gesture features (e.g., prone or supine), orientation features (e.g., head-first or feet-first), and behavior features (e.g., move or turn). One or more of these body features are indicative of the patient position, such as but not limited to a head-first supine position, a feet-first prone position, a head-first left lateral recumbent position, or a feet-first right lateral recumbent position, etc.

In some embodiments, characteristic features include position markers placed on or near an imaging object. Particularly, in some embodiments, position markers may be placed on the patient support or other system components. In some embodiments, system components of distinctive exterior features may serve as positional markers, such as a coil or other accessories of the system. According to the present disclosure, position markers may be of any distinctive combination of shape, color and/or texture. Exemplary embodiments include black, white, grayscale, colorful, fluorescent; standard geometrical shapes such as circle, oval, triangle, square, trapezium, diamond, rhombus, parallelogram, rectangle, pentagon, hexagon, heptagon, oblong, octagon, nonagon, decagon or the like; symbols such as star, heart, moon, arrow, stripe, ladder, or the like; icons or images such as a teddy bear, a national flag, or the like; letters, barcodes, and characters; textures such as rough, smooth, heat-absorbing, heat-reflective, etc.

Characteristic features captured on camera may be recognized due to their characteristic color, shape, texture, spatial relationship, or any combination thereof. Various methods or algorithms may be used. For shape extraction, methods or algorithms that can be used include multi-scale edge detection, wavelets and Chamfer matching, low level feature selection, feature extraction by shape matching, flexible shape extraction, LBP, GLDM, GLRLM, Haralick, and Gabor texture features. For color extraction, methods or algorithms that can be used include color-histogram, color sets, or color matrix. For texture extraction, methods or algorithms that can be used include structural approach, signal processing method, geometric method, model technique, or statistical technique. Special relationship extraction can be performed by extracting features after segmenting images either according to colors or targets in the images or segmenting images into several regular slave modules. Methods or algorithms that can be used in connection with the present disclosure also include other machine vision algorithms currently available or to be developed in the future.

In step 1103, characteristic features are recognized. Various methods or algorithms may be used. For example, in some embodiments, an extracted feature is compared to a pre-stored reference feature for a match. If a match is found, the extracted feature is recognized and related information is recorded; otherwise, the extracted feature is ignored. Exemplary embodiments of algorithms that can be used in connection with the present disclosure include Principal component analysis using eigenfaces, Linear discriminate analysis, Elastic bunch graph matching using the FisherFace algorithm, the hidden Markov model, the multilinear subspace learning using tensor representation, the neuronal motivated dynamic link matching, 3D model-based algorithms, recognition, skin texture analysis, thermal cameras, skeletal-based algorithms, appearance-based models, or other methods currently available or to be developed in the future.

In step 1104, control information is generated according to the recognized characteristic features. The control information may be automatically generated by a system or input by a system operator based on the result of imaging recognition. For example, in some embodiments, a system is configured to automatically select a particular imaging protocol based on a recognized patient position. In some embodiments, the system is configured to display the result of image recognition for a system operator to input control information. In some embodiments, generated control information is executed locally by the positioning system. In other embodiments, generated control information is transmitted to a system external to the positioning system (such as an imaging system or an HIS) for execution.

It should be noted that the above embodiments are provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 12:
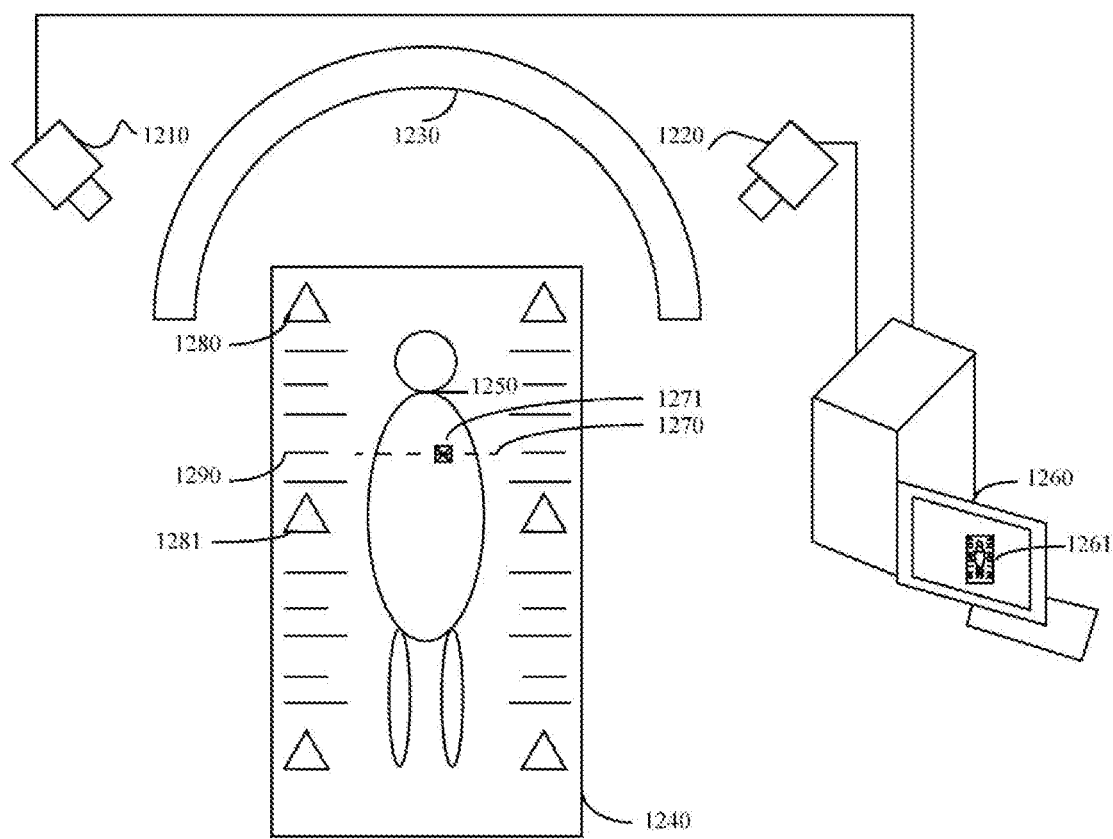
FIG. 12 illustrates an exemplary positioning procedure that is performed upon execution of the control information generated by the positioning system according to some embodiments of the present disclosure.

FIG. 12 illustrates an exemplary positioning procedure that is performed upon execution of the control information generated by the positioning system according to some embodiments of the present disclosure. Particularly, as shown in the figure, the imaging system comprises one or more cameras (1210, 1220), an imaging gantry 1230, a patient support 1240, and a display 1260. A patient 1250 lies on top of the patient support 1240. An image 1261 of the patient lying on the patient support is generated and shown on the display 1260.

Based on the displayed image, a system operator draws a line or an area across the displayed patient's chest, defining an edge of the ROI. For example, the system operator may draw an area 1721 on the displayed image. The positioning system 100 thus calculates corresponding physical position(s) of the line 1270 and/or the area 1721, and generates control information for moving and positioning the patient support 1240 relative to other components of the imaging system.

In some embodiments, the positioning system may comprise one or more position markers. For example, as shown in the figure, a set of position markers may be placed on the surface of the patient support 1240. Additionally or alternatively, as shown in the figure, a position marker 1271 may be placed on the patient's body.

In some embodiments, these position markers may assist the system operator in defining the ROI by providing reference points. Particularly, the displayed image may show the patient's position relative to one or more position markers. If one or more position markers are placed on the edge of the ROI, the system operator may simply draw the line across the markers.

In some embodiments, these position markers may further assist the positioning system in generating control information. Particularly, physical locations of one or more position markers may be known to the positioning system. For example, in some embodiments, a position marker may be zero position 900 as described in relation to FIG. 9, with respect to which the ROI's physical location may be calculated. In some embodiments, physical locations of position markers may directly correspond to distances by which the patient support 1240 should be moved. For example, a set of rough and fine markers may function as a distance ruler, with the space between adjacent markers representing a distance of 10 centimeters. Thus, if the positioning system, via for example machine vision, recognizes that the line 1270 crosses the fourth fine marker 1290 between the first and second rough markers 1280 and 1281, the positioning system generates control information, which upon execution, would move the patient support 1240 inward of the imaging gantry 1250 by 40 centimeters.

According to the present disclosure, position markers that may be used in connection with the present disclosure may be of any combination of colors, shapes, and/or textures. Exemplary embodiments include black, white, grayscale, colorful, or fluorescent; standard geometrical shapes such as circle, oval, triangle, square, trapezium, diamond, rhombus, parallelogram, rectangle, pentagon, hexagon, heptagon, oblong, octagon, nonagon, decagon, or the like; symbols such as star, heart, moon, arrow, strip, ladder, or the like; icons or images such as a teddy bear, a national flag or the like; letters, barcodes, and characters; textures such as rough, smooth, heat-absorbing, heart-reflecting, etc.

Further, in some embodiments, one or more position markers may be integrated with components of the imaging system. In some embodiments, components of the imaging system having characteristic features may serve the function of a position marker. For example, a head coil for MRI scanning wore by a patient may serve as a position marker. The positioning system, upon recognizing the characteristic shape of the coil, would generate control information that positions the patient's head and the coil in a targeted area.

In some embodiments, the control information is executed by the positioning system or an external system that communicates with the positioning system (such as a HIS). In some embodiments, execution of the control information involves a system operator to initiate an execution command (such as pressing a button). In other embodiments, execution of the control information is performed automatically by the system without human intervention, when certain conditions are met (such as immediately after control information is generated).

In various embodiments, the system executes control information to perform a positioning procedure that moves and positions an imaging object and one or more components of the imaging system relative to one another, such that the ROI is targeted in the corresponding imaging session. Particularly, system components moved and positioned during the positioning procedure include but are not limited to a support (e.g., a patient bed, a handle, etc.), a data acquisition device (e.g., an X-ray generator, a PET detector, etc.), a monitoring device (e.g., a camera, a lamp, etc.), a communication device (e.g., a microphone, a keypad, etc.), and a mechanical part (e.g., for carrying the system components, for adjusting a patient position, etc.). In some embodiments, during the positioning procedure, the system sends voice instruction for a patient to perform.

It should be noted that the above examples are provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 13:
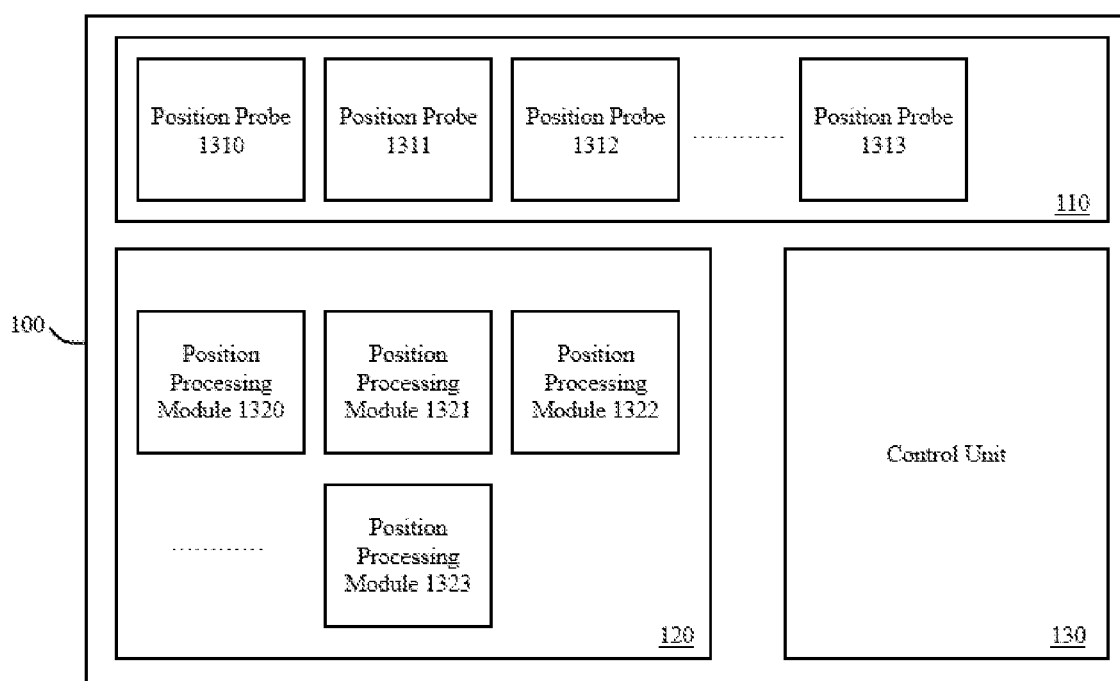
FIG. 13 is a block diagram of the positioning system according to some embodiments of the present disclosure.

FIG. 13 is a block diagram of the positioning system 100 according to some embodiments of the present disclosure. As shown in the figure, the positioning system 100 may comprise a position acquiring unit 110, a position processing unit 120, and a control unit 130 as described in connection with FIG. 1. Further, the position acquiring unit 110 may comprise one or more position probes, for example, position probe 1310, position probe 1311, position probe 1312, and position probe 1313. The position probes may be configured to communicate with one or more position sources.

The position processing unit 120 may comprise one or more position processing modules, for example, position processing module 1320, position processing module 1321, position processing module 1322, and position processing module 1323. The position processing module(s) may be configured to process the position information acquired by the position probe(s). Merely by way of example, the position of the position source(s) may be calculated by the position processing module(s). The control unit 130 may be configured to receive the position information calculated by the position processing unit 120, and control imaging system accordingly.

In some embodiments, ultrasound may be employed in the positioning system 100 to enable intercommunication between a position probe and a position source. For example, in some embodiments, the position source may be configured to emit ultrasound, and the position probe may be configured to receive the ultrasound signal. The distance between the position source and the position probe can be calculated based on the time delay between when the position source emits and when the position probe receives the signal. Thus, the position of a position source in a three-dimensional space may be calculated based on the distance between the position source and one or more position probes of known locations in the three-dimensional space, depending on relative spatial relationships between the position source and the position probe(s).

In some embodiments, the positioning system 100 may use alternative non-contact distance sensors to measure a distance between a position source and a position probe. For example, in some embodiments, infrared sensors or laser sensors may be used to measure the distance.

It should be noted that the description of the above embodiment of the positioning system is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 14:
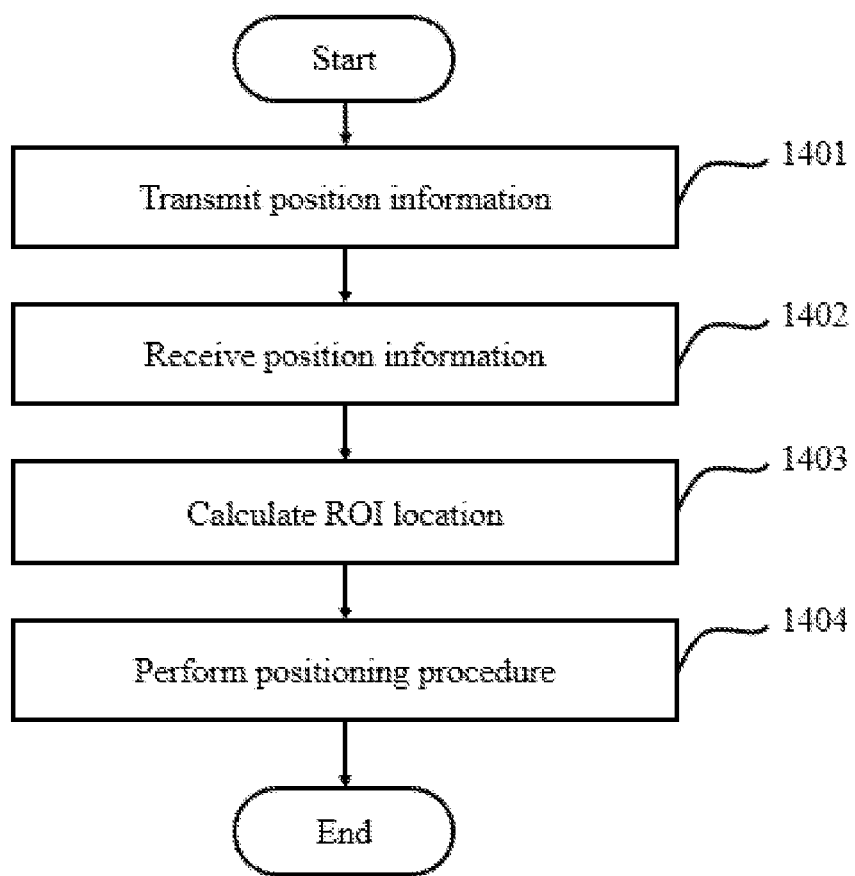
FIG. 14 is a flowchart illustrating an exemplary process of patient positioning according to some embodiments of the present disclosure.

FIG. 14 is a flowchart illustrating an exemplary process of patient positioning according to some embodiments of the present disclosure.

In step 1401, position information may be transmitted. The position information may be an ultrasound signal, a laser signal or an infrared signal, or the like, or any combination thereof.

In step 1402, the position information may be received. For example, in some embodiment, the position information may be received by an ultrasound sensor, a laser sensor, an infrared sensor, or the like, or any combination thereof.

In some embodiments, the positioning system may continuously monitor a patient's status by analyzing the position information. For example, in some embodiments, a position source may be placed on or near an ROI of a patient's body. Thus, the position information becomes indicative of the ROI's position. Accordingly, in some embodiments, in step 1403, the ROI's position may be calculated based on the position information received in step 1402. Merely by way of example, in some embodiments, location of a position source and thus the ROI can be calculated based on the distance between the position source and one or more position probes with known locations.

In step 1404, the imaging system may be controlled according to the ROI's position as calculated in step 1403. In some embodiments, the imaging system may be configured to monitor the status of a patient, including but not limited to monitoring the instant position of an ROI of the patient's body. In some embodiments, the positioning system may automatically adjust the location of the patient's body in real time, after the ROI's position is changed.

It should be noted the description above is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 15:
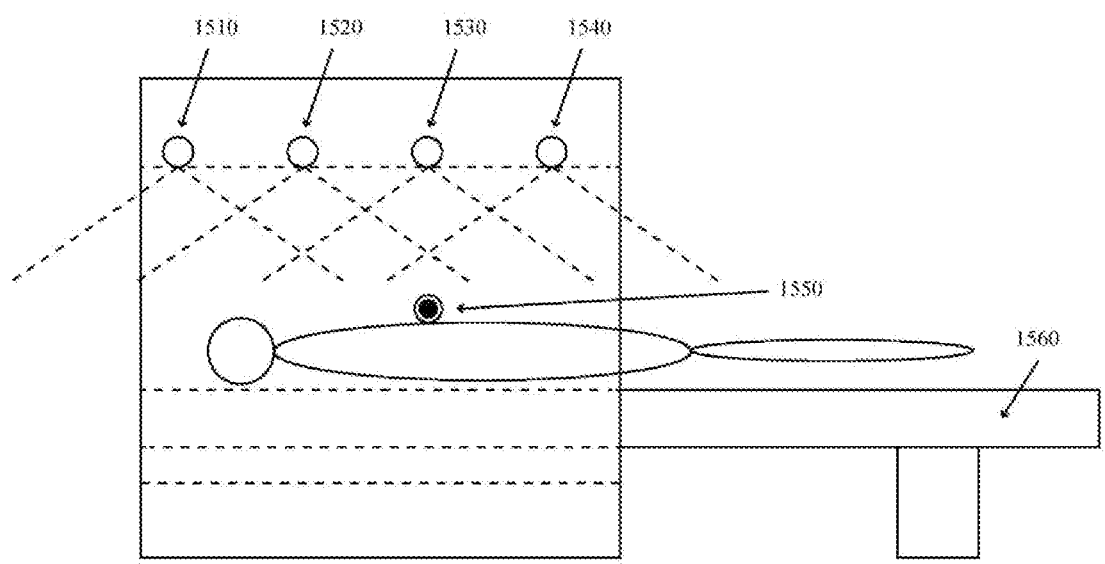
FIG. 15 illustrates the positioning system according to some embodiments of the present disclosure.

FIG. 15 is an illustration of the positioning system 100 according to some embodiments of the present disclosure. As shown in the figure, the positioning system 100 is equipped with multiple position probes (1510, 1520, 1530, 1540) for monitoring the status of a patient lying in the imaging system 1560. A position source 1550 is placed on the patient's body near an ROI that is to be targeted during imaging. The position source 1550 communicates with each of the position probes (1510, 1520, 1530, 1540), and the distance between the position source 1550 and each of the position probes (1510, 1520, 1540, 1540) can be measured.

Figure 16:
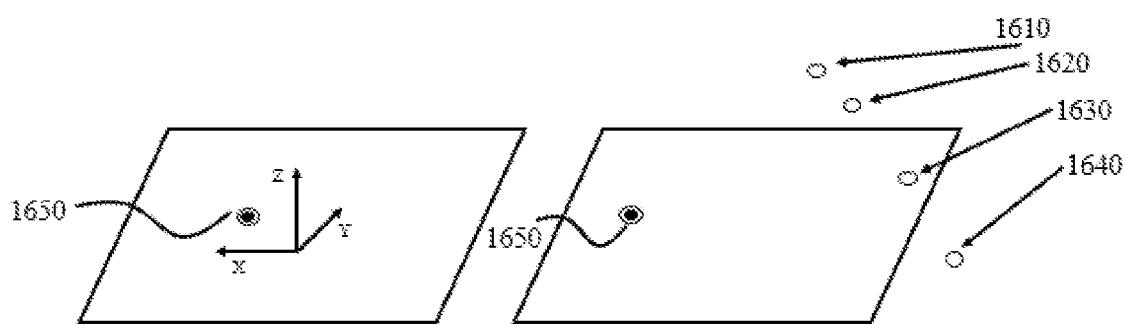
FIG. 16 illustrates a coordinate system that can be used to calculate the location of the position source in a three-dimensional space.

FIG. 16 illustrates a coordinate system that can be used to calculate the location of the position source 1650 in a three-dimensional space. As shown in the figure, set an xyz coordinate system where the position source 1650 can be treated as a point in the x-y plane. The multiple position probes (1610, 1620, 1630, 1640) can be treated as scattered points in the coordinate system, which may or may not in the x-y plane. In various embodiments, the multiple position probes (1610, 1620, 1630, 1640) may or may not share a same line or share a same plane in the xyz coordinate system.

Figure 17:
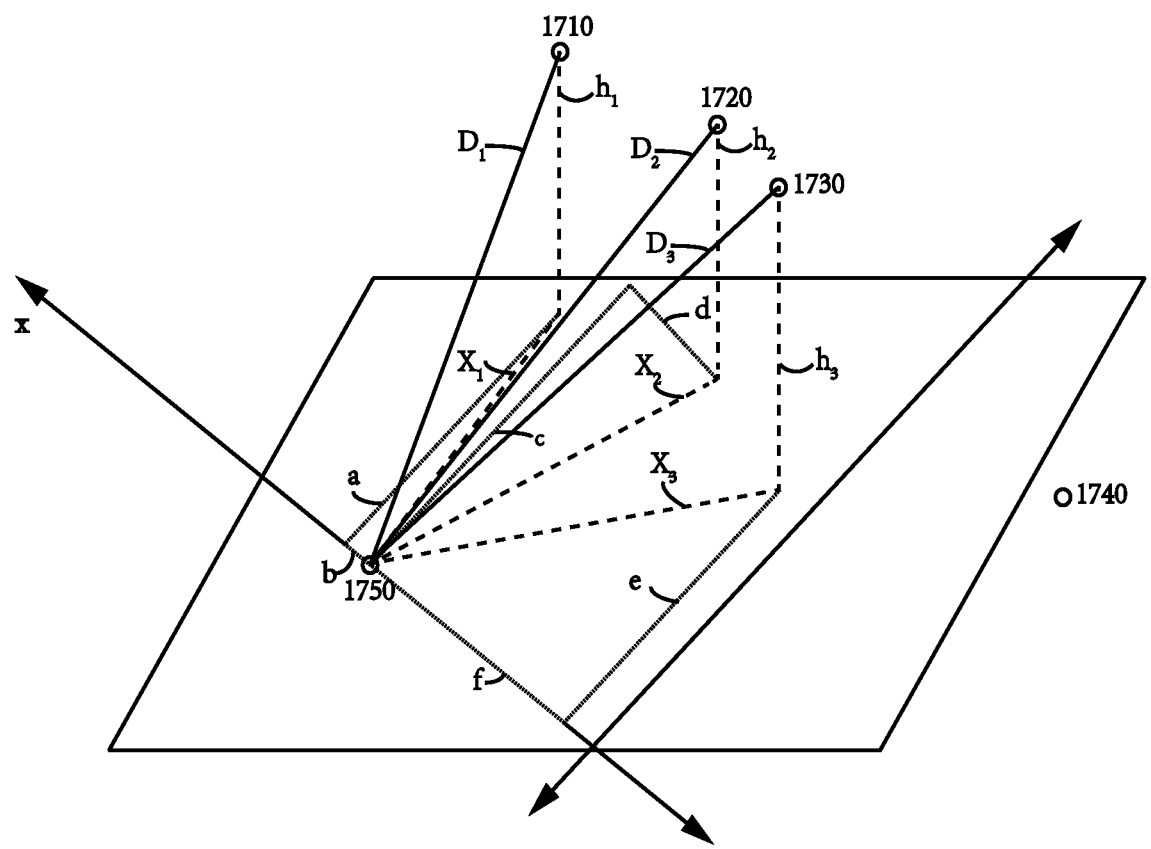
FIG. 17 illustrates one exemplary method for calculating the location of a position source in a three-dimensional space according to some embodiments of the present disclosure.

FIG. 17 illustrates one exemplary method for calculating the location of a position source in a three-dimensional space according to some embodiments of the present disclosure. As shown in the figure, the position source 1750 is in the x-y plane and may move along the x-axis. In various embodiments, one or more position probes (e.g., 1710, 1720, 1730, 1740) may assume various positional relationships with respect to the position source 1750 and/or with respect to one another. One or more of the position probes (e.g., 1710, 1720, 1730, 1740) may or may not locate in the x-y plane.

In the figure, $D_1$, $D_2$, and $D_3$ respectively denote the distance between the position source 1750 and each of the position probes (1710, 1720, 1730); $h_1$, $h_2$, $h_3$ denote respectively the distance between the x-y plane and each of the position probes (1710, 1720, 1730). $X_1$, $X_2$, and $X_3$ denote respectively the projection of $D_1$, $D_2$, and $D_3$ on the x-y plane; a, c, e denote respectively the y-axis component of $X_1$, $X_2$ and $X_3$; and f denote respectively the x-axis component $X_1$, $X_2$, and $X_3$. In some embodiments, a patient support as described in connection with FIG. 1 moves along the x-axis. Therefore, $$D_1^2 = a^2 + b^2 + h_1^2$$

$$D_2^2 = c^2 + d^2 + h_2^2$$

$$D_3^2 = e^2 + f^2 + h_3^2$$

$$c - a = \Delta_1$$

$$b + d = L2$$

$$b + f = \Delta_3$$

$$e - c = \Delta_4$$

$$h_1 - h_2 = \Delta_5$$

$$h_2 - h_3 = \Delta_6$$

$$h_3 - h_1 = \Delta_7 \qquad \text{(Equation Set 1)}$$

where $\Delta_1, \Delta_2, \Delta_3, \Delta_4, \Delta_5, \Delta_6, \Delta_7$ are known design constants. By solving Equation Set 1, three-dimensional location of the position source 1750 can be obtained.

In some embodiments, the one or more position probes (e.g., 1710, 1720, 1730, 1740) may share a same plane which is in parallel with the x-y plane in the xyz coordinate system as described in connection with FIG. 16. Under this circumstance, $h_1$ may equal to $h_2$ and $h_2$ may equal to $h_3$. Thus $\Delta_5$, $\Delta_6$ and $\Delta_7$ all equal to 0.

In some embodiments, the perpendicular height to the x-y plane of the position probes (1710, 1720, 1730) may differ. In this case at least one of $\Delta_5$, $\Delta_6$, $\Delta_7$ is nonzero.

In some embodiments, during operation of the imaging system, location of the position source may be moved. In some embodiments, the positioning system is configured to measures $D_1$, $D_2$, and $D_3$ constantly, for example via ultrasound distance sensing. Thus, location of the position source 1750 may be monitored in real time.

In some embodiments, each position probe has a signal range, within which range it communicates with a position source. In some embodiments, the system automatically establishes communication between a moving position source and a position probe, once the source enters the signal range of the probe. In some embodiments, the system automatically terminates communication between a moving position source and a position probe, once the source leaves the signal range of the probe.

In some embodiments, multiple position probes are arranged such that their respective signal ranges overlap. Particularly, in some embodiments, when a moving position source leaves the signal range of a position probe, it simultaneously enters the signal range of another position probe. In some embodiments, the positioning system is configured to use different sets of location probes for monitoring the instant location of a moving position source. For example, as shown in FIG. 17, if position source 1750 moves towards position probe 1740 and away from position probe 1710, it may establish communication with probe 1740 while terminating communication with probe 1710. Accordingly, the positioning system would then calculate a location of source 1750 based on known locations of probes 1720, 1730 and 1740.

It should be noted the description above is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 18:
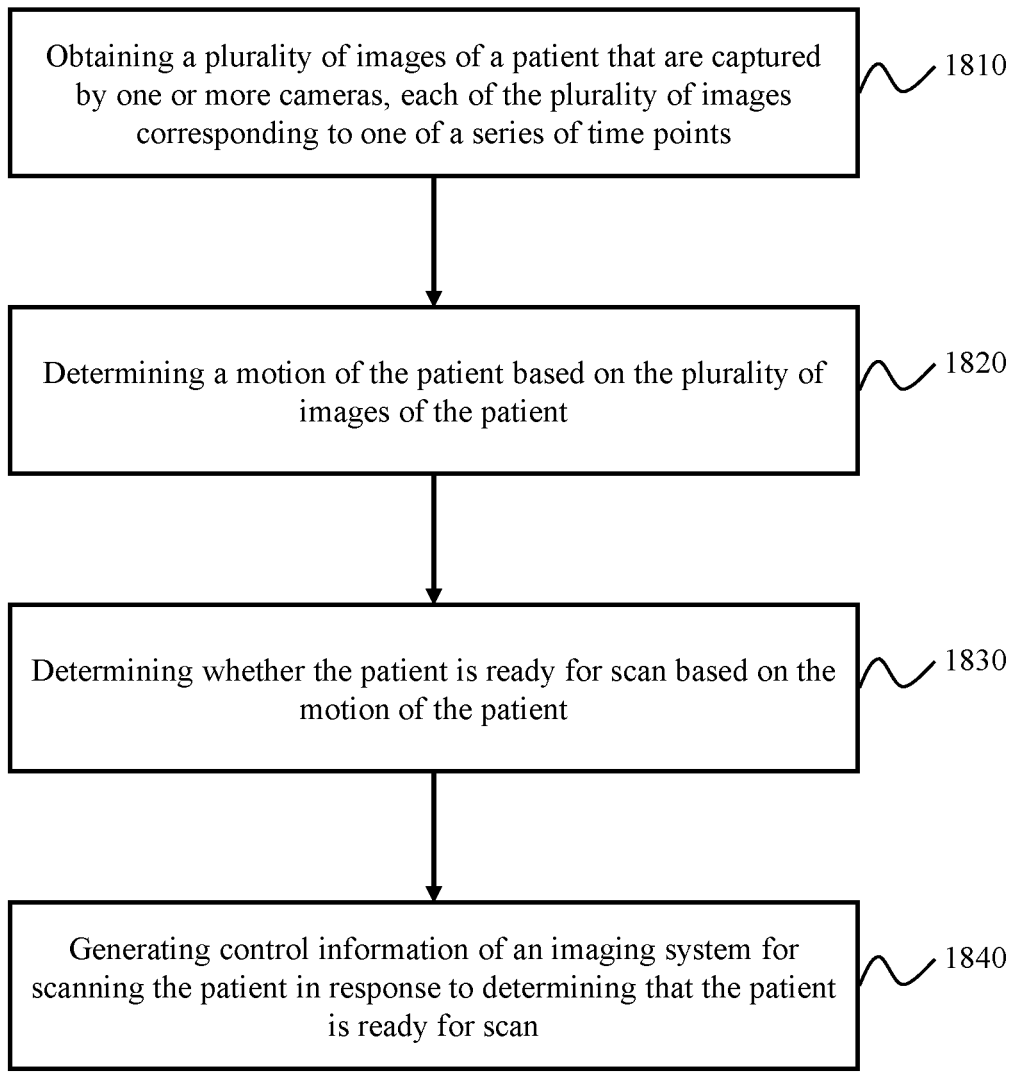
FIG. 18 is a flowchart illustrating an exemplary process for automated patient readiness detection according to some embodiments of the present disclosure.

FIG. 18 is a flowchart illustrating an exemplary process for automated patient readiness detection according to some embodiments of the present disclosure. In some embodiments, process 1800 may be executed by the positioning system 100. For example, the process 1800 may be implemented as a set of instructions (e.g., an application) stored in a storage device. In some embodiments, the position processing unit 120 and/or the control unit 130 may execute the set of instructions and may accordingly be directed to perform process 1800.

In some embodiments, an imaging system (e.g., the imaging system 170) may be used to perform a scan on a patient (or a portion thereof). The patient may be placed on a patient support. One or more cameras may be directed at the patient and configured to capture image data of the patient. The camera(s) may include any suitable device that is capable of capturing image data of the patient, e.g., a digital camera, an analog camera, an RGB sensor, an RGB-D sensor, a 3D scanner, a range device, a structured light scanner, a TOF device, or the like, or any combination thereof. In some embodiments, at least one of the camera(s) may include a position source and a position probe, wherein the position source and the position probe may be communicated with each other via a non-contact communication in between. The position source may be configured to emit a positioning signal (e.g., an ultrasound signal, an infrared signal, or a laser signal). The position probe may be configured to receive the positioning signal emitted by the position source via the non-contact communication in between. The position signal may be used to monitor an instant location of an ROI of the patient. More descriptions regarding the camera(s) may be found elsewhere in the present disclosure. See, e.g., FIG. 3 and the relevant descriptions thereof.

In some embodiments, before the scan, the patient may lie on the patient support and be required to get ready for scan (e.g., keep still). After the patient is in a still or substantially still state, the patient support may be directed to move the patient to a target position (e.g., where an ROI of the patient is coincident with an isocenter of the imaging system 170) for scan. Conventionally, an operator (e.g., a doctor) of the imaging system may need to observe the patient and determine whether the patient is ready for scan, which may be inefficient and susceptible to human error or subjectivity.

In order to improve the efficiency and/or accuracy of patient readiness detection, the process 1800 may be performed to automatically determine whether the patient is ready for scan based on image data captured by the camera(s). For example, the process 1800 may be performed when and after the patient lies down on the patient support continuously or intermittently (e.g., periodically) so that the patient's readiness may be tracked in real-time or intermittently. As another example, after the patient lies on the patient support, the operator may roughly determine that the patient is ready for scan and actuate the position processing unit 120 and/or the control unit 130 to perform the process 1800.

In 1810, the position processing unit 120 (e.g., the acquisition module 323) may obtain a plurality of images of the patient that are captured by the camera(s). Each of the plurality of images may correspond to one of a series of time points (or referred to as a time series).

In some embodiments, each of the camera(s) may be directed to capture a set of images from its perspective at the series of time points. The time interval between each pair of consecutive time points of the time series may be fixed or unfixed. For example, each camera may be directed to capture an image in every time unit (e.g., 0.1 seconds, 0.2 seconds, 0.3 seconds, etc.). The position processing unit 120 may obtain the one or more sets of images (or a portion thereof) from the camera(s) as the plurality of images via a wireless connection and/or a wired connection between the position processing unit 120 and the camera(s). Alternatively, the one or more sets of images may be previously captured by the camera(s) and stored in a storage device (e.g., a storage device of the imaging system, an external storage device, etc.). The position processing unit 120 may retrieve the one or more sets of images (or a portion thereof) from the storage device as the plurality of images.

An image captured by a camera may include a representation of the entire patient or a portion of the patient (e.g., an upper part, a lower part, or the chest of the patient). The image may be a 2D image or a 3D image. The image may be a color image (e.g., an RGB image), a point-cloud image, a depth image, a mesh image, an IR image, or any other type of image.

In 1820, the position processing unit 120 (e.g., the determination module 324) may determine a motion of the patient over the series of time points based on the plurality of images of the patient.

As used herein, a motion of the patient may be measured by one or more motion parameters, such as a moving distance, a moving direction, a moving trajectory, a change of a posture, a change of a posture representation, or the like, or any combination thereof, of the patient (or a portion thereof). A moving distance may include a pixel distance in the image domain and/or an actual distance in the physical space. A posture of the patient may reflect one or more of a position, a pose, a shape, a size, etc., of the patient (or a portion thereof). A posture representation of the patient refers to a quantitative expression that describes the posture of the patient. For example, the posture representation may include one or more parameter values relating to the posture of the patient and/or a vector (or matrix) that encodes the one or more parameter values. Exemplary parameter values relating to the posture of the patient may include a coordinate of a portion (e.g., the head, the neck, a hand, a leg, and/or a foot) of the patient in a certain coordinate system, a joint angle of a joint (e.g., a shoulder joint, a knee joint, an elbow joint, and/or an ankle joint) of the patient, a shape and/or a size of a portion of the patient, a height of the entire patient or a portion (e.g., the upper body, the lower body) of the patient, or the like, or any combination thereof.

The motion of an object (e.g., the patient or a portion thereof) over the time series may include a motion of the object from a first time point of the time series to a second time point after the first time point of the time series, wherein the first and second time points may be any two different time points of the time series. The first and second time points may be a pair of consecutive time points (i.e., there is no intermediate time point between the first and second time points) or a pair of inconsecutive time points (i.e., there are one or more intermediate time points between the first and second time points) among the time series. For example, it is assumed that the time series includes time points T1 to Tn, wherein n refers to any positive integer greater than 1. The motion of the object over the time series may include a motion of the object from T1 to Tn, which may be determined based on the images captured at T1 and Tn. As another example, the motion of the object over the time series may include a motion of the object between each pair of consecutive time points of the time series, e.g., a motion from T1 to T2, a motion from T2 to T3, . . . , and a motion from T(n−1) to Tn. The motion of the object between a pair of consecutive time points may be determined based on images captured at the pair of consecutive time points.

In some embodiments, the position processing unit 120 may determine the motion of the patient over the time series by tracking the motion of one or more characteristic regions of the patient over the time series based on the images. A characteristic region of the patient refers to a predetermined representative body region of the patient. Exemplary characteristic regions of a patient may include one or more anatomical joints, a shoulder, an ankle, the waist, a knee, a groin, or the like, or any combination thereof. Additionally or alternatively, the position processing unit 120 may generate a plurality of mesh models representative of the patient based on the images, and determine the motion of the patient over the time series based on the mesh models. A mesh model of the patient may include a plurality of vertices, edges, and faces that define a 3D shape of the patient (or a portion thereof). More descriptions regarding the determination of the motion of the patient may be found elsewhere in the present disclosure. See, e.g., FIG. 19 and the relevant descriptions thereof.

In some embodiments, the one or more cameras may include a plurality of cameras directed at the patient from different views. For each of the cameras, the position processing unit 120 may determine a motion of the patient from the camera's view based on the set of images captured by the camera. Additionally or alternatively, the sets of images captured by the cameras may be composed to generate a plurality of panoramic images, wherein each of the panoramic images may correspond to a specific time point of the time series and generated based on images captured by the cameras at the specific time point. For example, a referent pattern may be placed on the patient support, and a panoramic image corresponding to the specific time point may be generated based on representations of the reference pattern in the images captured by the cameras at the specific time point. The position processing unit 120 may determine the motion of the patient based on the panoramic images. For illustration purposes, the following descriptions are described with reference to the determination of the patient's motion based on the original images, and not intended to limit the scope of the present disclosure.

In 1830, the position processing unit 120 (e.g., the determination module 324) may determine whether the patient is ready for scan based on the motion of the patient.

In some embodiments, the patient may be regarded as being ready for scan if he/she is in a still or substantially still state over the time series. For example, the position processing unit 120 may determine whether the motion of the patient exceeds a threshold T'1. If the motion of the patient does not exceed the threshold T'1, the position processing unit 120 may determine that the patient is in a still state over the time series and ready for scan, and the process 1800 may proceed to operation 1840. If the motion of the patient exceeds the threshold T'1, the position processing unit 120 may determine that the patient is not is a still state and not ready for scan. The threshold relating to the motion may have a preset value or a value that can be dynamically adjusted by the position processing unit 120 according to different conditions. For example, the position processing unit 120 may determine different thresholds corresponding to different portions of the patient, and the motion of a specific portion of the patient may be compared with the threshold corresponding to the specific portion.

In some embodiments, as described in connection with 1820, the motion of the patient may be measured by various motion parameters, such as a moving distance, a change of a posture, a change of a posture representation, or the like, or any combination thereof. Each of the motion parameters may have a corresponding threshold value. For example, the moving distance of the patient may be compared with a threshold distance. As another example, the change of the posture representation of the patient may include a change of a parameter value relating to the posture of the patient (e.g., a joint angle change of a joint). The change of the parameter value relating to the posture of the patient may be compared with a threshold of the parameter value (e.g., a threshold angle relating to the joint). The position processing unit 120 may determine that the motion of the patient exceeds the threshold T'1 if a motion parameter exceeds a corresponding threshold value.

In some embodiments, the position processing unit 120 may generate a prompt message regarding the result of the determination as to whether the patient is ready for scan. The prompt message may be transmitted to one or more components of the positioning system 100 and/or the imaging system 170, such as the displaying device 140, the control console 150, etc. The promoting message may be in the form of, for example, a text message, a voice message, a graphic message, etc. For example, if it is determined that the patient is not ready for scan, the position processing unit 120 may transmit a prompt message to the imaging system 170. In response to the prompt message, the imaging system 170 may generate an audio instruction to remind the patient to keep still. As another example, if it is determined that the patient is ready for scan, the position processing unit 120 may transmit a prompt message to an operator of the imaging system 170 to confirm the determination result. In some embodiments, in response to determining that the patient is not ready for scan, the position processing unit 120 may perform operations 1810 to 1830 again until it is determined that the patient is ready for scan.

In 1840, in response to determining that the patient is ready for scan, the control unit 130 (e.g., the control information module 330) and/or the position processing unit 120 may generate control information of the imaging system for scanning the patient.

In some embodiments, the control unit 130 may determine the position of an ROI of the patient based on at least one of the plurality of images obtained in operation 1810. An ROI of the patient refers to a region of the patient in an image. The ROI may correspond to a specific physical portion (e.g., a tissue, an organ) of the patient. The position of the ROI refers to the position of the specific physical portion corresponding to the ROI in the physical space. For example, the control unit 130 may identify an area representing the chest of the patient from the at least one image, and determine the position of the chest based on the identified area.

In some embodiments, the ROI may be identified from an image manually, semi-automatically, or automatically. In an automatic approach, a contour of the ROI may be identified from an image automatically by a computing device (e.g., the control unit 130) without user intervention. For example, the contour of the ROI may be segmented from the image automatically according to a contour detection algorithm, such as a Sobel edge detection algorithm, a Canny edge detection algorithm, a phase congruency-based algorithm, or the like, or a combination thereof. In a semi-automatic approach, the contour of the ROI may be identified from an image by a computing device with user intervention. For example, the contour identification may be performed by the computing device based on a contour detection algorithm in combination with information provided by a user. Exemplary user intervention in a semi-automatic approach for the contour detection may include providing a parameter relating to the contour detection algorithm, providing a position parameter relating to the ROI, making an adjustment to or confirming a preliminary contour detection performed by the computing device, providing instructions to cause the computing device to repeat or redo the contour detection, etc. In a manual approach, the contour of the ROI may be identified from an image according to an instruction provided by a user. For example, via a user interface implemented on, e.g., control console 150 as illustrated in FIG. 1, a user may mark the contour in the image(s).

In some embodiments, the position of the ROI may be determined based on at least one of the plurality of images obtained in operation 1810 in combination with information related to the patient to be scanned. For example, the information may include an imaging protocol or a user input that specifies the specific portion of the patient to be scanned. The information may be a default setting of the imaging system or inputted manually by a user. Alternatively, the information, e.g., the imaging protocol may be determined by the imaging system automatically.

Based on the position of the ROI of the patient, the control unit 130 may generate the control information of the imaging system for positioning the patient. For example, the control information may include an instruction to move one or more components of the positioning system 100 and/or the imaging system 170 (e.g., the patient support 160) such that the ROI can be targeted (e.g., an isocenter of the ROI is coincident with an isocenter of the imaging system). The instruction may involve various parameters related to the movement of the system components, such as a moving distance, a moving direction, a moving speed, etc.

In some embodiments, the control unit 130 may determine the position of the ROI based on one or more images other than the images obtained in 1810. For example, the position of the ROI may be determined based on another image captured by the camera(s) or another camera (e.g., a current image of the patient captured by the camera(s) or another camera). As another example, the position of the ROI may be determined based on a projection image of the patient, wherein the projection image may be a simulated image of the patient from a view different from the view of the camera(s). Merely by way of example, the images obtained in operation 1810 may include 3D image data corresponding to a first view with respect to the patient. The control unit 130 may obtain a position of each of the camera(s) relative to the patient support. The control unit 130 may generate the projection image data corresponding to a second view with respect to the patient based on the 3D image data and the position of each of the camera(s) relative to the patient support. The second view may be different from the first view.

The control unit 130 may further determine the position of the ROI of the patient based on the projection image data. More descriptions regarding the determination of the position of the ROI based on projection image data may be found elsewhere in the present disclosure. See, e.g., FIG. 20 and the relevant descriptions thereof.

It should be noted that the above description regarding the process 1800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1800 may be accomplished with one or more additional operations not described and/or without one or more of the operations discussed above. For example, the process 1800 may include an additional operation in which the control unit 130 may perform a positioning procedure to position the patient according to the control information generated in 1840. Additionally or alternatively, the order of the process 1800 may not be intended to be limiting.

In some embodiments, the position processing unit 120 may obtain an image of the patient captured by a camera and determine the posture of the patient based on the representation of the patient in the image. The position processing unit 120 may further determine whether the posture of the patient is an unstable posture. Normally, the patient may be unstable and tend to move when he/she holds some specific postures, for example, holds the patient support with hands, bends the elbows, raises legs, or the like. If the patient holds an unstable posture, the position processing unit 120 may determine that the patient is not ready for scan, or vice versa.

Figure 19:
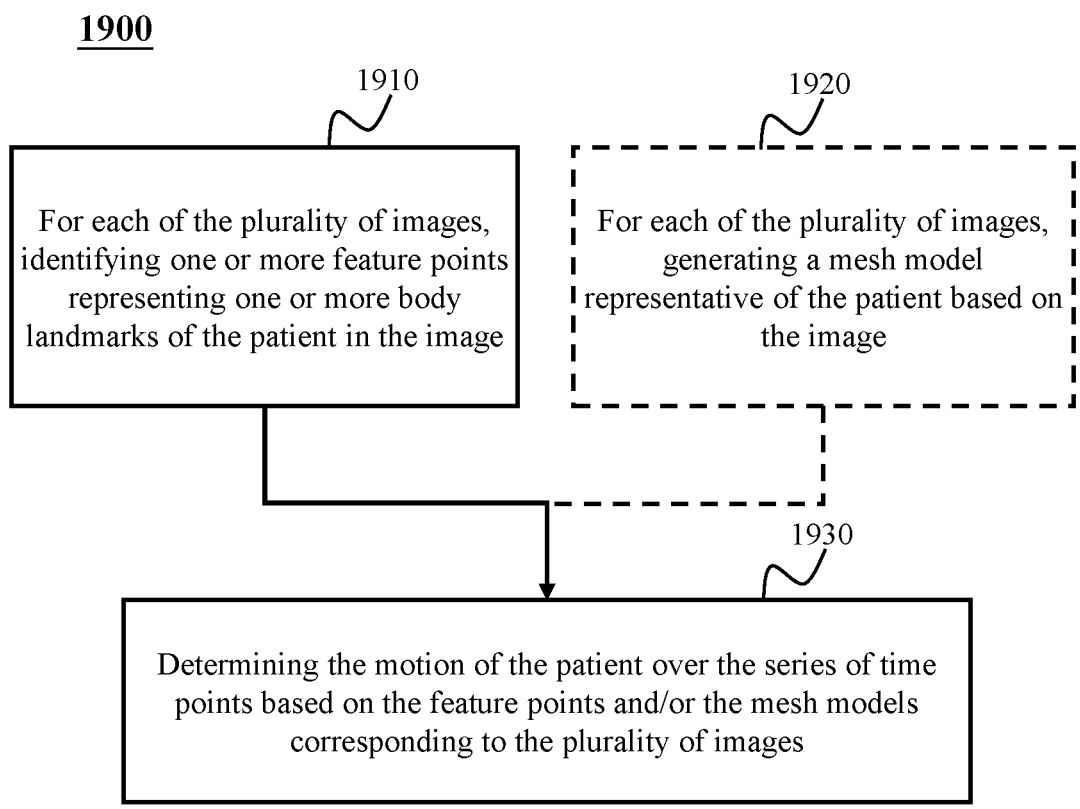
FIG. 19 is a flowchart illustrating an exemplary process for determining a motion of a patient based on a plurality of images of the patient according to some embodiments of the present disclosure.

FIG. 19 is a flowchart illustrating an exemplary process for determining a motion of a patient over a time series based on a plurality of images of the patient according to some embodiments of the present disclosure. In some embodiments, the process 1900 may be an exemplary embodiment of operation 1820 as described in connection with FIG. 18. In some embodiments, process 1900 may be executed by the positioning system 100. For example, the process 1900 may be implemented as a set of instructions (e.g., an application) stored in a storage device. In some embodiments, the position processing unit 120 (e.g., one or more modules illustrated in FIG. 3) may execute the set of instructions and may accordingly be directed to perform process 1900.

In 1910, for each of the images, the position processing unit 120 (e.g., the determination module 324) may identify one or more feature points representing one or more body landmarks of the patient in the image.

The body landmark(s) may include one or more representative body regions of the patient, such as one or more anatomical joints, a shoulder, an ankle, the waist, a knee, a groin, or the like, or any combination thereof. The feature point(s) identified in an image may include one or more areas corresponding to the body landmark(s) in the image.

A feature point may be identified from an image manually, semi-automatically, or automatically. For example, the image of the patient may be transmitted to a terminal device (e.g., the displaying device 140, the control console 150) for display. Via a user interface implemented on the terminal device, a user may annotate the feature point in the displayed image. As another example, the position processing unit 120 may identify the feature point in the image automatically without user intervention. The automatic identification of the feature point(s) may be performed according to an image analysis technique (e.g., an image segmentation algorithm, an object recognition algorithm), a machine learning based technique (e.g., a trained neural network model for feature point detection), or the like, or any combination thereof. As yet another example, the feature point may be determined semi-automatically by the position processing unit 120 with user intervention. For example, a user may provide a parameter relating to a parameter relating to the image analysis technique and/or a position parameter relating to a feature point. As another example, the user may make an adjustment to or confirm a preliminary feature point identification performed by the position processing unit 120. The position processing unit 120 may identify the feature point based on the image analysis technique in combination with the parameter and/or adjustment provided by the user.

In some embodiments, after 1910, the process 1900 may proceed to 1930 in which the position processing unit 120 may determine the motion of the patient over the time series based on the feature point(s) identified in each image.

For example, the position processing unit 120 may determine a motion of the body landmark(s) over the time series based on the identified feature points. Taking the left ankle as an exemplary body landmark, a first pixel representing the left ankle may be identified from an image corresponding to a first time point, and a second pixel representing the left ankle may be identified from an image corresponding to a second time point after the first time point. The position processing unit 120 may determine a pixel distance between the first and second pixels, and designate the pixel distance or an actual distance corresponding to the pixel distance as the motion of the left ankle over the time series. The position processing unit 120 may further determine the motion of the patient over the time series based on the motion of the body landmark(s) over the time series. For example, if there are a plurality of body landmarks, the position processing unit 120 may determine a maximum motion or an average motion of the body landmarks as the motion of the patient.

In some alternative embodiments, the position processing unit 120 may perform 1920 instead of 1910 in the process 1900. In 1920, for each of the plurality of images, the position processing unit 120 may generate a mesh model representative of the patient based on the image. In 1930, the position processing unit 120 may determine the motion of the patient over the time series based on the mesh models corresponding to the plurality of images.

A mesh model of the patient determined based on an image may be a 3D model reflecting a posture (e.g., the position, the shape, or the size) of the patient when the image is captured. The mesh models corresponding to the images may be used to track a change in the posture of the patient over the time series. In some embodiments, operation 1910 may be performed to roughly determine a local motion of one or more body landmarks of the patient. The mesh models may represent the patient in a 3D space and be used to determine a global motion of the patient precisely.

In some embodiment, the position processing unit 120 may generate a mesh model of the patient based on an image according to one or more mesh generation techniques, such as a Triangular/Tetrahedral (Tri/Tet) technique (e.g., an Octree algorithm, an Advancing Front algorithm, a Delaunay algorithm, etc.), a Quadrilateral/Hexahedra (Quad/Hex) technique (e.g., a Trans-finite Interpolation (TFI) algorithm, an Elliptic algorithm, etc.), a hybrid technique, a parametric model based technique, a surface meshing technique, or the like, or any combination thereof.

After the mesh models are generated, the position processing unit 120 may track the motion of the patient over the time series based on the mesh models. For example, each of the mesh models may include a collection of vertices, edges, and faces that defines a 3D shape of the patient. The position processing unit 120 may identify at least one element (e.g., a vertex, an edge, and/or a face) from each of the mesh models. Further, the position processing unit 120 may determine the motion of the patient based on the identified at least one element in each mesh model by, for example, determining a position difference between the identified elements of different mesh models.

As another example, for each of the plurality of images, the position processing unit 120 may determine a posture representation of the patient based on the corresponding mesh model of the patient. A posture representation corresponding to an image may be used to quantitatively measure the posture of the patient when the image is captured. Merely by way of example, the posture representation may include one or more parameter values relating to the posture of the patient and/or a vector (or matrix) that encodes the one or more parameter values.

The position processing unit 120 may further determine the motion of the patient over the time series based on the posture representations of the patient corresponding to the plurality of images. For example, a first posture representation of the patient may be determined based on the mesh model corresponding to an image captured at a first time point of the time series, and a second posture representation of the patient may be determined based on a mesh model corresponding to an image captured at a second time point of the time series. The first posture representation may include one or more first parameter values relating to the posture of the patient at the first time point, and the second posture representation may include one or more second parameter values relating to the posture of the patient at the second time point. The position processing unit 120 may determine a difference between the first and second parameter values as the motion of the patient. As another example, the first posture representation may include a first vector relating to the posture of the patient at the first time point, and the second posture representation may include a second vector relating to the posture of the patient at the second time point. The position processing unit 120 may determine a difference between the first and second vectors as the motion of the patient.

In some embodiments, the position processing unit 120 may determine a posture representation of the patient base on a mesh model in combination with at least one of a patient model, a posture representation determination model, or a kinematic chain model.

As used herein, a patient model refers to a model (e.g., a 3D mesh model) representing a reference patient holding a reference posture, wherein the reference posture may have a known posture representation (referred to as a reference representation for clarity). A posture representation determination model refers to a neural network model that is configured to receive image data of a patient holding a certain posture as an input, and output a representation of the certain posture. A kinematic chain model may have a similar function to the posture representation determination model and be configured to output a digitized representation of the posture of the patient based on an input image of the patient. According to the kinematic chain model, a human include a plurality of kinematic chains, each of which may represent a plurality of body segments connected by joints. For example, a leg may be represented by a kinematic chain, and the motion of different segments of the leg (e.g., the upper leg, the lower leg, the knee, and the muscles on the leg) may be constrained by their connections to each other. Merely by way of example, in some embodiments, the kinematic chain model may include a convolutional neutral network, a fully connected layer, and a kinematic layer. The convolutional neutral network may be used to extract features from an input image of a patient. The fully connected layer may be used to output one or more motion parameters of the patient (e.g., a position and/or a rotation angle of a bone of the patient). The kinematic layer may map the motion parameter(s) to one or more joint parameters of the patient, such as a joint location and/or a joint angle of the patient. As another example, the kinematic chain model may include an encoder block and a hierarchical kinematic pose regressor block. The encoder block may be configured to extract one or more features of patient from the input image of the patient. The hierarchical kinematic pose regressor block may be configured to estimate parameters (e.g., a joint angle and/or shape) of the kinematic chains of the patient based on the feature(s) extracted by the encoder block.

For example, the position processing unit 120 may obtain a plurality of patient models from, e.g., a storage device of the positioning system 100 or a vendor that provides and/or maintains such patient model. The plurality of patient models may include patient models representing a same reference patient holding different poses and/or at different positions. Additionally or alternatively, the plurality of patient models may include patient models representing different reference patients, for example, different reference patients having different body shapes (e.g., heights and/or weights) and/or holding different poses. The position processing unit 120 may determine a matching degree (or similarity degree) between the mesh model and each of the plurality of patient models. Further, the position processing unit 120 may select a patient model that has the highest matching degree with the mesh model among the patient models. The position processing unit 120 may then determine the posture representation of the patient corresponding to the mesh model based on the reference posture representation of the selected patient model.

As another example, the position processing unit 120 may obtain the posture representation determination model or the kinematic chain model from, e.g., a storage device of the positioning system 100 or a vendor that provides and/or maintains such posture representation determination model or the kinematic chain model. The position processing unit 120 may input the mesh model into the posture representation determination model or the kinematic chain model, and the posture representation determination model or the kinematic chain model may output the posture representation corresponding to the mesh model. More descriptions regarding the patient model and/or the posture representation determination model may be found in U.S. patent application Ser. No. 16/656,511 entitled "SYSTEMS AND METHODS FOR PATIENT POSITIONING" filed on Oct. 17, 2019, the contents of which are hereby incorporated by reference. More descriptions regarding the kinematic chain model may be found in, a literature entitled "Deep Kinematic Pose Regression" published on "ECCV Workshop on Geometry Meets Deep Learning" on 2016, the contents of which are hereby incorporated by reference.

In some embodiments, both the operations 1910 and 1920 may be performed in the process 1900, e.g., simultaneously or in sequence. In 1930, the position processing unit 120 may determine the motion of the patient based on the feature points and the mesh models. For example, the motion of the patient may be measured by one or more motion parameters determined based on the feature points and one or more motion parameters determined based on the mesh models.

In some embodiments, the position processing unit 120 may determine the motion of the patient by performing a two-level determination. In a first-level determination, the position processing unit 120 may track the motion of the body landmark(s) and determine whether the motion of the at least one body landmark exceeds a threshold T'2. The threshold T'2 may have a preset value (e.g., 1 mm, 3 mm, 5 mm, etc.) or a value that can be dynamically adjusted by the position processing unit 120 according to different conditions. If the motion of the at least one body does not exceed the threshold T'2, the position processing unit 120 may determine that the patient is ready for scan. In order to further confirm the result of the first-level determination, the position processing unit 120 may perform a second-level determination. In the second-level determination, the position processing unit 120 may determine the motion of the patient based on the mesh models and determine whether the patient is ready for scan based on the motion. The two-level determination may improve the accuracy the automatic readiness detection.

In some embodiments, operations 1910 and 1920 may be performed based on a same set of images or different sets of images captured by the camera(s). Merely by way of example, the camera(s) may be directed to capture images of the patient and transmit the images to the position processing unit 120 continuously or intermittently (e.g., periodically). The position processing unit 120 may perform operation 1910 based on a first set of images of the patient captured by the camera(s) at a first time series to perform a first-level determination. If it is determined that the patient is ready to scan according to the first level determination, the position processing unit 120 may perform operation 1920 based on a second set of images of the patient newly captured by the camera(s), so that an instant (or real-time) state of the patient may be monitored. For example, the second set of images may be captured at a second time series that include one or more time points after the first time series.

It should be noted that the above description regarding the process 1900 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1900 may be accomplished with one or more additional operations not described and/or without one or more of the operations discussed above. Additionally, the order of the process 1900 may not be intended to be limiting.

Figure 20:
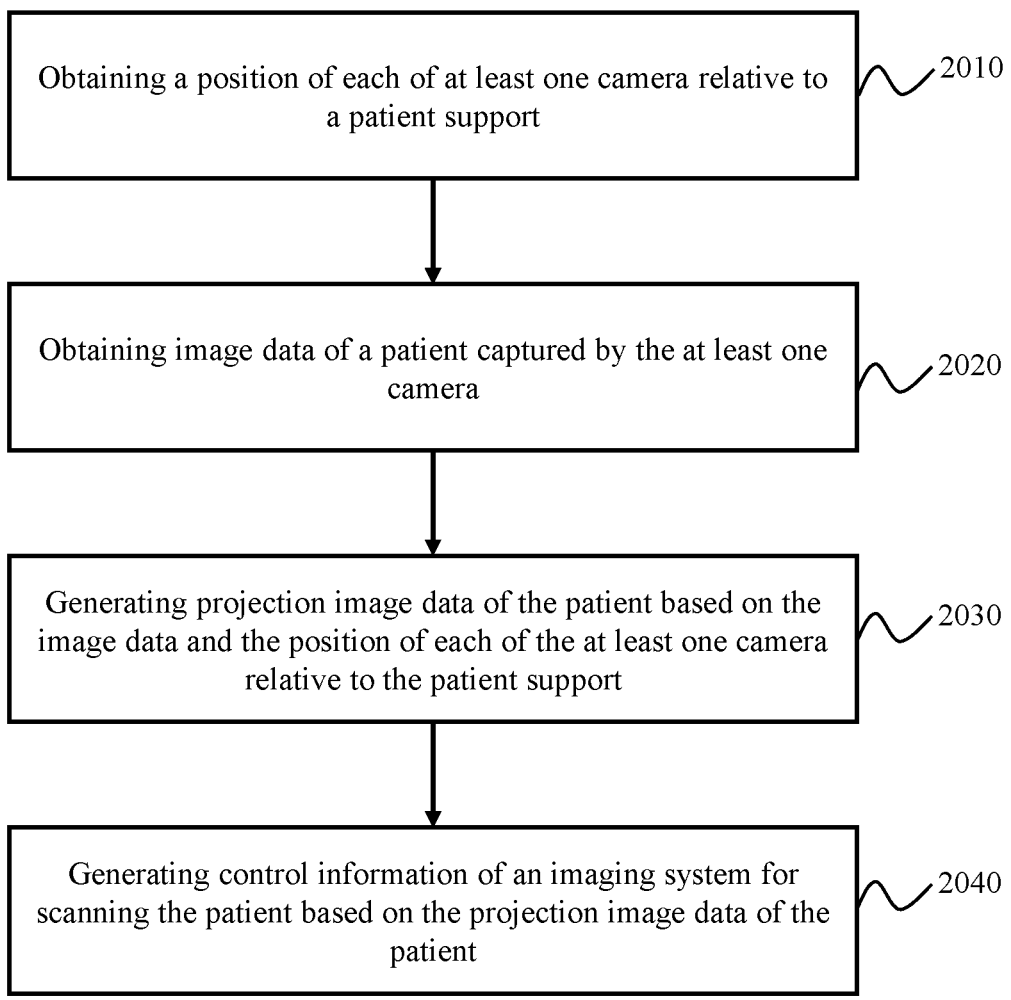
FIG. 20 is a flowchart illustrating an exemplary process for scanning a patient in an imaging system according to some embodiments of the present disclosure.

FIG. 20 is a flowchart illustrating an exemplary process for scanning a patient in an imaging system according to some embodiments of the present disclosure. In some embodiments, the process 2000 may be executed by the positioning system 100. For example, the process 2000 may be implemented as a set of instructions (e.g., an application) stored in a storage device. In some embodiments, the position processing unit 120 (e.g., one or more modules illustrated in FIG. 3) and/or the control unit 130 may execute the set of instructions and may accordingly be directed to perform process 2000.

In some embodiments, the imaging system (e.g., the imaging system 170) that scans the patient may include one or more cameras directed at the patient and a patient support for supporting the patient. The camera(s) may be configured to obtain image data of the patient. More descriptions regarding the camera(s) and the patient support may be found elsewhere in the present disclosure. See, e.g., FIG. 1 and relevant descriptions thereof. Before the scan starts, the patient may need to be moved to a position so that an ROI of the patient may be targeted. Conventional positioning techniques may rely on a maker (e.g., a laser pointer) to mark the ROI, which may be inefficient and inaccurate. The process 2000 may be performed to position and scan the patient based on the image data of the patient captured by the camera(s), which may improve the efficiency and precision of patient positioning.

In some embodiments, the process 2000 may be performed based on a position of each of the camera(s) relative to the imaging system. As used herein, a position of a camera relative to the imaging system may include a position of the camera relative to, for example, the patient support of the imaging system, the gantry of the imaging system, an isocenter of the imaging system, or the like, or any combination thereof. For illustration purposes, the present disclosure is described with reference to the position of the camera relative to the patient support. This is not intended to limit the scope of the present disclosure, and the process 2000 may be performed based on the position of each of the camera(s) relative to any other component of the imaging system.

In 2010, the position processing unit 120 (e.g., the acquisition module 323) may obtain a position of each of the camera(s) relative to the patient support.

A position of a camera relative to the patient support may be represented in various forms. For example, the position of the camera relative to the patient support may be represented by a distance between the camera and the patient support (e.g., a specific point of the patient support). As another example, the position of the camera relative to the patient support may be represented by an angle between an image plane of the camera and an upper surface of the patient support (i.e., a surface where the patient is placed).

As yet another example, the position of the camera relative to the patient support may be represented by a transformation relationship between a first coordinate system with respect to the camera and a second coordinate system with respect to the patient support. The transformation relationship between the first coordinate system and the second coordinate system may indicate a relationship between first coordinates of one or more points in the first coordinate system and their corresponding second coordinates in the second coordinate system. Taking a specific point as an example, the transformation relationship may indicate a transformation relationship between a first coordinate of the specific point in the first coordinate system and a second coordinate of the specific point in the second coordinate system. The second coordinate of the specific point may be determined based on the first coordinate of the specific point and the transformation relationship between the first coordinate and the second coordinate of the specific point.

In some embodiments, the first coordinate system with respect to the camera may be associated with one or more equipment parameters of the camera. For example, the first coordinate system may be an orthogonal coordinate system including an $X_1$ axis, a $Y_1$ axis, and a $Z_1$ axis. The origin of the first coordinate system may be coincident with an optical center of the camera, the $X_1$ may be parallel to a horizontal direction of an image plane of the camera, the $Y_1$ may be parallel to a vertical direction of the image plane of the camera, and the $Z_1$ may be perpendicular to the image plane of the camera.

The second coordinate system with respect to the patient support may be used to define a position of an object on the patient support or in the imaging system. For example, the second coordinate system may be a coordinate system 180 as shown in FIG. 1. The coordinate system 180 may be an orthogonal coordinate system including an X axis, a Y axis, and a Z axis. The origin of the coordinate system 180 may be coincident with, for example, a central point of the upper surface of the patient support, a rotation center of the gantry of the imaging system 170, etc. The X axis and the Z axis may define a horizontal plane parallel to the upper surface of the patient support. The Y axis may be perpendicular to the X-Z plane. As illustrated in FIG. 1, the positive X direction along the X axis may be from the left side to the right side of the imaging system 170 seen from the direction facing the front of the imaging system 170; the positive Y direction along the Y axis shown in FIG. 1 may be from the lower part to the upper part of the imaging system 170; and the positive Z direction along the Z axis may be a direction in which the object is moved out of a scanning channel of the imaging system 170.

In some embodiments, the transformation relationship between the first coordinate system and the second coordinate system may be presented in the form of a table recording the first coordinates of the one or more points in the first coordinate system and their corresponding second coordinates in the second coordinate system. Alternatively, the transformation relationship between the first coordinate system and the second coordinate system may be described in a transformation matrix or a transformation function. Merely by way of example, the transformation relationship may be described in the form of a matrix M (e.g., a 4*4 matrix). The matrix M may indicate rotations around the $X_1$ axis, the $Y_1$ axis, and the $Z_1$ axis, and translations along the $X_1$ axis, the $Y_1$ axis, and the $Z_1$ axis. A coordinate of a specific point in the second coordinate system may be determined by multiplying the matrix M with a coordinate of the specific point in the first coordinate system.

In some embodiments, the position of a camera relative to the patient support may be determined by the position processing unit 120 by performing one or more operations of process 2000 as described in connection with FIG. 20. Alternatively, the position of the camera relative to the patient support may be previously determined by the position processing unit 120 or another computing device, and stored in a storage device (e.g., a storage device of the positioning system 100, an external storage device, etc.). The position processing unit 120 may access the storage device and acquire the position of the camera relative to the patient support. Merely by way of example, the position of the camera relative to the patient support may be calibrated when the imaging system is installed. For example, when the imaging system is installed, the process 2100 may be performed by a computing device of the positioning system 100 or a vendor of the imaging system 170 (or the positioning system 100) to determine the position of the camera with respect to the patient support. Optionally, the position of the camera relative to the patient support may be updated intermittently, for example, at regular intervals (e.g., 1 month, 3 months, 6 months, 1 year, etc.).

In 2020, the position processing unit 120 (e.g., the acquisition module 323) may obtain image data of the patient captured by the camera(s).

The image data of the patient may include one or more images and/or any related image data (e.g., scan data, projection data, etc.) of the entire patient or a portion of the patient. The one or more images may include one or more 2D images and/or one or more 3D images of the patient. The image data may include color image data, point-cloud data, depth image data, mesh data, IR image data, or the like, or any combination thereof, of the patient.

In some embodiments, the image data of the patient may include 3D image data of the patient. The 3D image data may be captured by a 3D camera capable of capturing 3D image data. The acquisition module 323 may obtain the 3D image data from the 3D camera or a storage device that stores the 3D image data (e.g., a storage device of the positioning system 100, an external storage device, etc.). Alternatively, the camera(s) may include a plurality of 2D cameras configured to capture 2D image data of the patient from different perspectives. The position processing unit 120 may obtain the 2D image data from the cameras, and generate the 3D image data based on the 2D image data. Alternatively, the 3D image data may be previously generated based on the 2D image data and stored in a storage device (e.g., a storage device of the positioning system 100, an external storage device, etc.). The position processing unit 120 may retrieve the 3D image data from the storage device.

In some embodiments, the image data of the patient may correspond to a first view with respect to the patient. The first view with respect to the patient refers to a view from which the patient is captured in the image data. For example, the first view with respect to the patient may be perpendicular to the upper surface of the patient support (e.g., the first view may be along the negative Y-axis direction that is perpendicular to the X-Z of the coordinate system 180 as shown in FIG. 1). In other words, the image data may present a front view of the patient (or a portion thereof). As another example, the first view with respect to the patient may be at an acute angle (e.g., 45°) to the upper surface of the patient support.

In 2030, the position processing unit 120 (e.g., the determination module 324) may generate projection image data of the patient based on the image data and the position of each of the camera(s) relative to the patient support.

The projection image data may include one or more projection images and/or any related projection data of the patient rendered from the image data. A projection image of the patient may be a 2D projection image or a 3D projection image. A projection image may be of a same type as or a different type from the image data of the patient as described in connection with 2020. The projection image data may include color image data, point-cloud data, depth image data, mesh data, IR image data, or the like, or any combination thereof, of the patient.

Each of the projection image(s) may correspond to a second view with respect to the patient, which is different from the first view. For a projection image, a second view with respect to the patient refers to a view from which the patient is projected in the projection image or a view from which the image data is rendered to generate the projection. For example, the first view with respect to the patient may be perpendicular to the upper surface of the patient support, and the image data may be the front view of the patient. The second view may be parallel to the upper surface of the patient support (e.g., the second view may be along the X-axis direction that is perpendicular to the Y-Z of the coordinate system 180 as shown in FIG. 1). That is, the image data may be rendered from a view parallel to the upper surface of the patient support to generate a projection image which is a side view of the patient. As another example, the first view with respect to the patient may be parallel to or at an acute angle (e.g., 45°) to the upper surface of the patient support. The second view may be perpendicular to the upper surface of the patient support (e.g., the second view may be along the negative Y-axis direction of the coordinate system 180). That is, the image data may be rendered from a view perpendicular to the upper surface of the patient support to generate a projection image which is a front view of the patient.

In some embodiments, a plurality of projection images of the patient may be generated by rendering the image data from different second views. Merely by way of example, a projection image showing a left side of the patient (e.g., from a direction facing the left hand of the patient) and another projection image showing a right side of the patient (e.g., from a direction facing the right hand of the patient) may be generated.

In some embodiments, for a camera, the position processing unit 120 may determine a position of a corresponding virtual camera having a second view based on the position of the camera relative to the patient support. A virtual camera refers to a function of a computer program (e.g., an animation software) that may work and behave in a same way as or a similar way to a real camera in real-world situations. The computer program may be used to determine how an object may be rendered based on the position and/or the angle of the virtual camera. For example, the image data may represent the front view of the patient. To generate a projection image representing a side view of the patient, the virtual camera may be placed at a same (or substantially same) height as the patient support or above the patient support for a certain distance, and face a side of the patient. The position of such virtual camera in the first coordinate system with respect to the camera may be determined based on the position of the camera with respect to the patient support. The position processing unit 120 may further generate a projection image by rendering the image data based on the position and the view of the virtual camera. In such cases, the projection image may be represented in the first coordinate system with respect to the camera.

Alternatively, the position processing unit 120 may determine a position of the virtual camera in the second coordinate system with respect to the patient support. Merely by way of example, the image data may be represented in the first coordinate system with respect to the camera. The position processing unit 120 may transform the image data into transformed image data in the second coordinate system. For example, the position processing unit 120 may transform the image data based on the transformation relation between the first coordinate system and the second coordinate system. To generate a projection image representing a side view of the patient, the virtual camera may be placed at a same (or substantially same) height as the camera or above the patient support for a certain distance, and face a side of the patient. That is, a Y-coordinate of the virtual camera in the second coordinate system may be same (or substantially same) as a Y-coordinate of the patient support or equal to a sum of the Y-coordinate of the patient support and the certain distance. The position processing unit 120 may further generate the projection image by rendering the image data based on the position and the view of the camera. In such cases, the projection image may be represented in the second coordinate system with respect to the patient support.

In some embodiments, the rendering of the image data and/or the transformed image data may be performed based on one or more image rendering techniques, for example, a rasterization technique, a ray casting technique, a ray-tracing technique, a radiosity technique, or the like, or any combination thereof. In some embodiments, the image data and/or the transformed image data may include 2D image data of the patient. The position processing unit 120 may estimate a 3D body contour of the patient based on the 2D image data, and generate the projection image data based on the estimated 3D body contour of the patient.

In 2040, the control unit 130 (e.g., the control information module 330) and/or the position processing unit 120 may generate control information of the imaging system for scanning the patient based on the projection image data of the patient. For illustration purposes, the implementation of operation 2040 performed by the control unit 130 is described hereinafter.

In some embodiments, the control unit 130 may determine a position of an ROI of the patient based on the projection image data. For example, the projection image data may represent a side view of the patient, the position of ROI may include coordinate(s) of one or more points of the ROI along the Y-axis in the second coordinate system with respect to the patient support. Optionally, the control unit 130 may determine the position of the ROI based on the projection image data in combination with the image data obtained in operation 2020. For example, the image data may represent a front view of the patient in the first coordinate system with respect to the camera. The control unit 130 may determine coordinate(s) of one or more points of the ROI in the X-Z plane in the second coordinate system based on the image data and the transformation relationship between the first and second coordinate systems. In this way, the control unit 130 may determine a 3D position of the ROI in the second coordinate system, which may improve the positioning precision. In some embodiments, the determination of the ROI's position based on the projection image data and/or the image data may be performed in a similar manner with that based on the at least one image as described in connection with 1840, and the descriptions thereof are not repeated here.

Based on the position of the ROI, the control unit 130 may generate the control information for positioning the patient. For example, the control information may include an instruction to move one or more components of the positioning system 100 and/or the imaging system 170 (e.g., the patient support 160 such that the physical portion can be targeted (e.g., an isocenter of the physical portion is coincident with an isocenter of the imaging system). More descriptions regarding the generation of the control information of the imaging system may be found elsewhere in the present disclosure. See, e.g., 1840 and relevant descriptions thereof.

It should be noted that the above description regarding the process 2000 is merely provided for the purposes of illustration, and not intended to limit the scope of the present disclosure. For persons having ordinary skills in the art, multiple variations and modifications may be made under the teachings of the present disclosure.

However, those variations and modifications do not depart from the scope of the present disclosure. In some embodiments, the process 2000 may be accomplished with one or more additional operations not described and/or without one or more of the operations discussed above. Additionally, the order of the process 2000 may not be intended to be limiting.

For example, the image data and the projection image data may represent the front view and the side view of the patient, respectively. The process 2000 may further include an operation in which the position processing unit 120 may combine the image data and the projection image data to generate a full-view image of the patient. As another example, the image data may include image data captured by a plurality of cameras that have overlapping fields of view. The position processing unit 120 may generate panoramic image data relating to the patient by composing the image data captured by the cameras. The position processing unit 120 may further generate panoramic projection image data of the patient based on the panoramic image data and the position of each of the camera(s) relative to each other. Alternatively, for each camera, the position processing unit 120 may generate projection image data based on the image data captured by the camera based on the position of the camera relative to the patient support. The position processing unit 120 may further generate panoramic projection image data by composing the projection image data corresponding to the cameras. The generation of the panoramic image data and/or the panoramic projection image data may be performed in a similar manner with that of a panoramic image as described in connection with 402, and the descriptions thereof, are not repeated herein.

In some embodiments, image data of the patient may be captured continuously or intermittently (e.g., periodically) for patient readiness detection. Merely by way of example, the image data may include a plurality of images, each of which may correspond to one time point of a time series. In 2030, for each of the images, the position processing unit 120 may generate a projection image based on the image, thereby generating a plurality of projection images corresponding to the time series. The position processing unit 120 may further determine a motion of the patient over the series of time points based on the projection images or a combination of the projection images and the original images. For example, one or more feature points representing one or more body landmarks of the patient may be identified from each of the projection images to track the motion of the body landmark(s) over the time series. As another example, a plurality of mesh models may be generated based on the projection images, and the motion of the patient over the time series may be tracked based on the mesh models. Based on the motion of the patient, the position processing unit 120 may determine whether the patient is ready for scan, and further generate the control information of the imaging system for scanning the patient in response to determining that the patient is ready for scan. In some embodiments, the patient readiness detection based on the projection images may be performed in a similar manner with that described in connection with FIG. 18, and the descriptions thereof are not repeated here.

Figure 21:
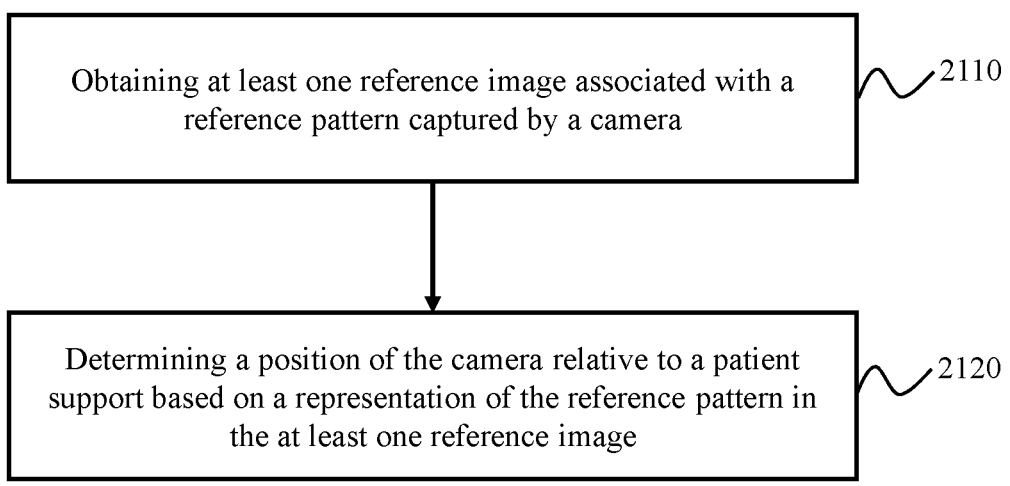
FIG. 21 is a flowchart illustrating an exemplary process for determining a position of a camera relative to a patient support according to some embodiments of the present disclosure.

FIG. 21 is a flowchart illustrating an exemplary process for determining a position of a camera relative to a patient support according to some embodiments of the present disclosure. In some embodiments, process 2100 may be an exemplary embodiment of operation 2010 as described in connection with FIG. 20. In some embodiments, the process 2100 may be executed by the positioning system 100. For example, the process 2100 may be implemented as a set of instructions (e.g., an application) stored in a storage device. In some embodiments, the position processing unit 120 and/or the control unit 130 may execute the set of instructions and may accordingly be directed to perform the process 2100. In some embodiments, the process 2100 may be performed by a system of a vendor that provides and/or maintains the camera (or the positioning system 100 or the imaging system 170), wherein the system of the vendor is different from the positioning system 100. For illustration purposes, the following descriptions are described with reference to the implementation of the process 2100 by the position processing unit 120, and not intended to limit the scope of the present disclosure.

In some embodiments, the position of the camera relative to the patient support may be determined based on a reference pattern placed on the patient support. As described elsewhere in this disclosure (e.g., FIGS. 7A to 7C and the relevant descriptions), the reference pattern may include any combination of colors, shapes, and/or textures. For example, the reference pattern may include a 3D reference pattern, a 2D reference pattern, a 1D reference pattern, or the like, or any combination thereof. A 3D reference pattern refers to a reference pattern that has a certain volume in a 3D space. Exemplary 3D reference patterns may include a cube, a cuboid, a cylinder, a prism, or the like. A 2D reference pattern refers to a reference pattern that is arranged on a 2D plane and has a certain size on the 2D plane. For example, the 2D reference pattern may include a checker, one or more boxes (e.g., the reference pattern 700 as shown in FIG. 7), or the like. A 1D reference pattern may include a plurality of points and/or a line. For example, the 1D reference pattern may include two points indicated by two cross-shaped graphs.

In some embodiments, the reference pattern and the patient support may form an integral assembly. Alternatively, the reference pattern may be mounted on the patient support via, for example, one or more screws, adhesives, glues, or the like. In some embodiments, one or more parameters, such as the shape, the size, and/or the position of the reference pattern may be previously measured and stored in a storage device (e.g., a storage device of the positioning system 100, an external storage device, etc.). Taking a 3D reference pattern as an example, parameters including the position of a vertex, an edge, a center point, and an angular point of the 3D reference pattern, a relative position of a point of the 3D reference pattern with respect to a reference point (e.g., a point with a known position on the patient support), a length of an edge of the 3D reference pattern, and/or an area of a surface of the 3D reference pattern, may be measured manually by an operator of the imaging system. As another example, the reference pattern may include two cross-shaped graphs disposed on the patient support. The imaging system 170 may be directed to scan the patient support and the cross-shaped graphs, and parameters of the two cross-shaped graphs (e.g., their coordinates in the second coordinate system, the distance between each other) may be determined based on an image generated from scan data acquired by the imaging system.

In 2110, the position processing unit 120 (e.g., the acquisition module 323) may obtain at least one reference image associated with the reference pattern captured by the camera.

A reference image refers to an image that includes a representation of at least a portion of the reference pattern.

The at least one reference image may be obtained from the camera or a storage device where the at least one reference image is stored.

The count of the reference image(s) may be any positive integer. For example, if the reference pattern is a 3D reference pattern, a single reference image of the 3D reference pattern may be obtained. If the reference pattern is a 2D reference pattern or a 1D reference pattern, a plurality of reference images may be obtained, wherein the plurality of reference images may be captured by the camera when the patient support is at different positions. Merely by way of example, for a 2D reference pattern, the camera may be directed to capture a first reference image associated with the 2D reference pattern when the patient support is at an initial position. Then, the patient support may be moved to another position by, for example, translating the patient support along the Y-axis of the second coordinate system (e.g., the coordinate system 180) to change its height and/or translating the patient support along the Z-axis direction to change its depth into the detection channel of the imaging system. The moving distance and the moving direction of the patient support from the initial position to the other position may be recorded for further analysis (e.g., for determining a position of the camera relative to the 2D reference pattern as described in connection with operation 2120). The camera may be directed to capture a second reference image after the patient support is moved to the other position. As another example, for a 1D reference pattern, the patient support may be moved multiple times, and the camera may be directed to capture a reference image every time after the patient support is moved.

In 2120, the position processing unit 120 (e.g., the determination module 324) may determine the position of the camera relative to the patient support based on the representation of the reference pattern in the at least one reference image.

In some embodiments, if the reference pattern is a 3D object, the position processing unit 120 may determine a first position of the camera relative to the reference pattern based on the representation of the reference pattern in the at least one reference image. Optionally, the determination of the first position may be performed further based on one or more parameters of the 3D reference pattern and one or more intrinsic parameters of the camera. Exemplary intrinsic parameters of the camera may include a focal length, a pixel aspect ratio, an image sensor format, a principal point, etc. For example, the representation of the 3D reference pattern in a reference image (e.g., the shape and/or size of the 3D reference pattern in the reference image) may be associated with the actual configuration of the 3D reference pattern, the intrinsic parameter(s) of the camera, and the position of the 3D reference pattern with respect to the camera. The position of the 3D reference pattern with respect to the camera may be estimated based on the parameter(s) of the 3D reference pattern, the representation of the 3D reference pattern in the reference pattern, and/or the intrinsic parameter(s) of the camera.

Further, the position processing unit 120 may obtain or determine a second position of the 3D reference pattern relative to the patient support. Based on the first position and the second position, the position processing unit 120 may then determine the position of the camera relative to the patient support. In some embodiments, the second position of the 3D reference pattern may be previously determined and stored in a storage device. For example, the 3D reference pattern may be placed on a predetermined position of the patient support. As another example, the second position of the 3D reference pattern relative to the patient support may be previously measured manually by an operator of the imaging system or determined based on the reference image. As yet another example, the position processing unit 120 may direct the imaging system to scan the 3D reference pattern to obtain a scan image of the 3D reference pattern. The position processing unit 120 may determine the second position based on the scan image of the 3D reference pattern.

In some embodiments, the reference pattern may be a 2D object or a 1D object, the position processing unit 120 may determine the position of the camera relative to the patient support by determining a transformation relationship between the first coordinate system and the second coordinate system based on a plurality of reference images. For example, the position processing unit 120 may determine a matrix (e.g., a 4*4 matrix as described in connection with 2010) representative of the transformation relationship based on the reference image. As another example, the reference pattern may include two or more cross-shaped graphs with known coordinates in the second coordinate system. The position processing unit 120 may extract a plurality of feature points representing the cross-shaped graphs from each of the reference images. The position processing unit 120 may further determine the transformation relationship based on the known coordinates of the cross-shaped graphs and the extracted feature points.

Using the reference pattern, the position of the camera relative to the patient support may be determined automatically based on the reference image(s), thereby improving the determination efficiency and the accuracy of the determined position, which in turn, may further improve the accuracy and efficiency of the patient positioning and/or diagnosis performed based thereon. For example, an operator of the imaging system may direct the positioning system 100 to determine or calibrate the position of the camera relative to the patient support intermittently (e.g., at regular intervals) or at any time as needed (e.g., when the position of the camera or the patient support is moved). In this way, precise projection image data and control information of the imaging system may be generated based on the newly updated position of the camera relative to the patient support. In addition, the reference pattern may have the advantages of simple structure, convenient manufacture, and low cost compared with other position measurement devices. In some embodiments, a 2D or 1D reference pattern may be utilized, and the transformation relationship between the first and second coordinate systems may be determined based on reference images of the 2D or 1D reference pattern. The efficiency of the position calibration of the camera may be further improved because the transformation relationship may be directly determined without determining a position of the camera relative to the reference pattern and a position of the reference pattern relative to the patient support.

It should be noted that the above description regarding the process 2100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 2100 may be accomplished with one or more additional operations not described and/or without one or more of the operations discussed above. Additionally, the order of the process 2100 may not be intended to be limiting.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer-readable media having computer-readable program code embodied thereon.

A computer-readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

What is claimed is:

1. A system for scanning a patient in an imaging system, the imaging system including at least one camera directed at the patient and at least one medical imaging device, comprising:
    at least one non-transitory storage device including a set of instructions; and
    at least one processor configured to communicate with the at least one non-transitory storage device, wherein when executing the set of instructions, the at least one processor is configured to direct the system to perform operations including:
    obtaining a plurality of images of the patient that are captured by the at least one camera, each of the plurality of images corresponding to one of a series of time points;
    determining, based on the plurality of images of the patient, a motion of the patient over the series of time points;
    determining, based on the motion of the patient, whether the patient is ready for scan; and
    in response to determining that the patient is ready for scan, generating control information of the at least one medical imaging device for performing a medical scan on the patient.

2. The system of claim 1, wherein the plurality of images of the patient include at least one of an RGB image, a depth image, or an infrared radiation (IR) image.

3. The system of claim 1, wherein the determining the motion of the patient based on the plurality of images of the patient includes:

for each of the plurality of images, identifying, in the image, at least one feature point representing at least one body landmark of the patient;

determining, based on the at least one feature point identified in each of the plurality of images, a motion of the at least one body landmark over the series of time points; and determining, based on the motion of the at least one body landmark, the motion of the patient over the series of time points.

4. The system of claim 3, wherein the determining the motion of the patient based on the motion of the at least one body landmark includes:

determining whether the motion of the at least one body landmark exceeds a threshold;

for each of the plurality of images, in response to determining that the motion of the at least one body landmark does not exceed the threshold, generating a mesh model representative of the patient based on the image; and determining, based on the mesh models corresponding to the plurality of images, the motion of the patient over the series of time points.

5. The system of claim 1, wherein the determining the motion of the patient based on the plurality of images includes:

for each of the plurality of images, generating a mesh model representative of the patient based on the image; and determining, based on the mesh models corresponding to the plurality of images, the motion of the patient over the series of time points.

6. The system of claim 5, wherein the determining the motion of the patient based on the mesh models corresponding to the plurality of images includes:

for each of the plurality of images, determining, based on the corresponding mesh model of the patient, a posture representation of the patient; and determining, based on the posture representations of the patient corresponding to the plurality of images, the motion of the patient over the series of time points.

7. The system of claim 6, wherein for each of the plurality of images, the determining the posture representation of the patient includes:

determining the posture representation of the patient based on at least one of a patient model, a posture representation determination model, or a kinematic chain model.

8. The system of claim 5, wherein the determining the motion of the patient based on the mesh models corresponding to the plurality of images includes:

for each of the plurality of mesh models corresponding to the plurality of images, identifying at least one vertex of the mesh model; and determining, based on the at least one vertex of each of the plurality of mesh models, the motion of the patient over the series of time points.

9. The system of claim 1, wherein the determining, based on the motion of the patient, whether the patient is ready for scan includes:

determining whether the motion of the patient exceeds a threshold; and in response to determining that the motion of the patient does not exceed the threshold, determining that the patient is ready for scan.

10. The system of claim 1, wherein the generating control information of the at least one medical imaging device for performing a medical scan on the patient includes:

determining, based on at least one of the plurality of images, a position of a region of interest (ROI) of the patient; and generating the control information of the at least one medical imaging device for performing the medical scan on the patient based on the position of the ROI of the patient.

11. The system of claim 10, wherein the patient is placed on a patient support, the at least one of the plurality of images include 3D image data corresponding to a first view with respect to the patient, and the determining a position of an ROI of the patient based on at least one of the plurality of images includes:

obtaining a position of each of the at least one camera relative to the patient support;

generating, based on the 3D image data and the position of the each of the at least one camera relative to the patient support, projection image data of the patient, the projection image data corresponding to a second view with respect to the patient different from the first view; and determining, based at least part on the projection image data, the position of the ROI of the patient.

12. A method implemented on a computing device having at least one processor and at least one non-transitory storage device for scanning a patient in an imaging system, the imaging system including at least one camera directed at the patient and at least one medical imaging device, the method comprising:

obtaining a plurality of images of the patient that are captured by the at least one camera, each of the plurality of images corresponding to one of a series of time points;

determining, based on the plurality of images of the patient, a motion of the patient over the series of time points;

determining, based on the motion of the patient, whether the patient is ready for scan; and in response to determining that the patient is ready for scan, generating control information of the at least one medical imaging device for performing a medical scan on the patient.

13. The method of claim 12, wherein the determining the motion of the patient based on the plurality of images of the patient includes:

for each of the plurality of images, identifying, in the image, at least one feature point representing at least one body landmark of the patient;

determining, based on the at least one feature point identified in each of the plurality of images, a motion of the at least one body landmark over the series of time points; and determining, based on the motion of the at least one body landmark, the motion of the patient over the series of time points.

14. The method of claim 13, wherein the determining the motion of the patient based on the motion of the at least one body landmark includes:

determining whether the motion of the at least one body landmark exceeds a threshold;

for each of the plurality of images, in response to determining that the motion of the at least one body landmark does not exceed the threshold, generating a mesh model representative of the patient based on the image; and determining, based on the mesh models corresponding to the plurality of images, the motion of the patient over the series of time points.

15. The method of claim 12, wherein the determining the motion of the patient based on the plurality of images includes:

for each of the plurality of images, generating a mesh model representative of the patient based on the image; and determining, based on the mesh models corresponding to the plurality of images, the motion of the patient over the series of time points.

16. The method of claim 15, wherein the determining the motion of the patient based on the mesh models corresponding to the plurality of images includes:

for each of the plurality of images, determining, based on the corresponding mesh model of the patient, a posture representation of the patient; and determining, based on the posture representations of the patient corresponding to the plurality of images, the motion of the patient over the series of time points.

17. The method of claim 16, wherein for each of the plurality of images, the determining the posture representation of the patient includes:

determining the posture representation of the patient based on at least one of a patient model, a posture representation determination model, or a kinematic chain model.

18. The method of claim 15, wherein the determining the motion of the patient based on the mesh models corresponding to the plurality of images includes:

for each of the plurality of mesh models corresponding to the plurality of images, identifying at least one vertex of the mesh model; and determining, based on the at least one vertex of each of the plurality of mesh models, the motion of the patient over the series of time points.

19. The method of claim 12, wherein the determining, based on the motion of the patient, whether the patient is ready for scan includes:

determining whether the motion of the patient exceeds a threshold; and in response to determining that the motion of the patient does not exceed the threshold, determining that the patient is ready for scan.

20. A non-transitory computer readable medium, comprising at least one set of instructions for scanning a patient in an imaging system, the imaging system including at least one camera directed at the patient and at least one medical imaging device, wherein when executed by at least one processor of a computing device, the at least one set of instructions causes the computing device to perform a method, the method comprising:

obtaining a plurality of images of the patient that are captured by the at least one camera, each of the plurality of images corresponding to one of a series of time points;

determining, based on the plurality of images of the patient, a motion of the patient over the series of time points;

determining, based on the motion of the patient, whether the patient is ready for scan; and in response to determining that the patient is ready for scan, generating control information of the at least one medical imaging device for performing a medical scan on the patient.

\* \* \* \* \*